(12) United States Patent
Kang et al.

(10) Patent No.: US 12,385,852 B2
(45) Date of Patent: Aug. 12, 2025

(54) GLASS INSPECTION EQUIPMENT AND METHOD OF GLASS INSPECTION

(71) Applicant: Samsung Display Co., Ltd., Yongin-si (KR)

(72) Inventors: Yunku Kang, Yongin-si (KR); Kitaek Kim, Yongin-si (KR); Sungmin Park, Yongin-si (KR); Janghoon Lee, Yongin-si (KR); Leegu Han, Yongin-si (KR)

(73) Assignee: SAMSUNG DISPLAY CO., LTD., Gyeonggi-Do (KR)

( * ) Notice: Subject to any disclaimer, the term of this patent is extended or adjusted under 35 U.S.C. 154(b) by 334 days.

(21) Appl. No.: 18/120,124

(22) Filed: Mar. 10, 2023

(65) Prior Publication Data

US 2024/0027363 A1 Jan. 25, 2024

(30) Foreign Application Priority Data

Jul. 25, 2022 (KR) .......................... 10-2022-0092006

(51) Int. Cl.
*G01N 21/958* (2006.01)
*G01N 21/88* (2006.01)
(Continued)

(52) U.S. Cl.
CPC ....... *G01N 21/958* (2013.01); *G01N 21/8806* (2013.01); *G01N 21/95* (2013.01); *G01N 33/386* (2013.01); *G01N 2021/8841* (2013.01)

(58) Field of Classification Search
CPC .. G01N 33/386; G01N 21/01; G01N 21/8851; G01N 21/8887; G01N 21/8806;
(Continued)

(56) References Cited

U.S. PATENT DOCUMENTS 5,973,776 A * 10/1999 Matsushita ........ G01N 21/8803
356/400
11,124,366 B2 * 9/2021 Tsai ....................... B65G 23/08
(Continued)

FOREIGN PATENT DOCUMENTS

CN 205015292 U * 2/2016
KR 20070103093 A * 10/2007
(Continued)

Primary Examiner — Gordon J Stock, Jr.
(74) Attorney, Agent, or Firm — CANTOR COLBURN LLP

(57) ABSTRACT

A glass inspection equipment includes a first transfer rail extending in a first direction, where a glass including first sides and second sides extending in a direction intersecting the first sides reciprocates in the first direction, a rotation part on the first transfer rail to rotate the glass, an edge inspection part on the first transfer rail to inspect the first and second sides of the glass, and a surface inspection part which inspects a surface of the glass, the edge inspection part inspects the first sides when the glass with the first sides arranged parallel to the first direction is transferred under the edge inspection part, and the edge inspection part inspects the second sides when the glass transferred through the edge inspection part is rotated by the rotation part and the glass with the second sides parallel to the first direction is transferred under the edge inspection part.

20 Claims, 28 Drawing Sheets

(51) Int. Cl.
*G01N 21/95* (2006.01)
*G01N 33/38* (2006.01)

(58) Field of Classification Search
CPC .... G01N 21/86; G01N 21/88; G01N 21/8803; G01N 21/8914; G01N 21/892; G01N 21/8921; G01N 21/8922; G01N 21/894; G01N 21/896; G01N 21/94; G01N 21/95; G01N 21/956; G01N 21/958; G01N 21/84; G01N 21/8901; G01N 2021/0106; G01N 2021/0187; G01N 2021/0193; G01N 2021/8887; G01N 2021/845; G01N 2021/8654; G01N 2021/8924; G01N 2021/8925; G01N 2021/8927; G01N 2021/8928; G01N 2021/8962; G01N 2021/8965; G01N 2021/8967; G01N 2021/9511; G01N 2021/9513; G01N 2021/9583; G01N 2021/9586; G01N 2021/0112; G01N 2021/8841; G06T 7/0004; G06T 7/001; G06T 2207/30108; B65G 21/10; B65G 47/22; B65G 2811/0621; B65G 2811/0626
See application file for complete search history.

(56) References Cited

U.S. PATENT DOCUMENTS

| | | | |
|---|---|---|---|
| 11,796,483 B2* | 10/2023 | Hu | G06T 7/0006 |
| 11,940,389 B2* | 3/2024 | Hu | G01N 21/8806 |
| 12,007,333 B2* | 6/2024 | Lee | G01N 21/958 |
| 2021/0254966 A1* | 8/2021 | Hur | G01B 5/0004 |
| 2022/0375061 A1* | 11/2022 | Hu | G06T 7/0004 |

FOREIGN PATENT DOCUMENTS

| | | | | |
|---|---|---|---|---|
| KR | 20110000542 A | * | 1/2011 | |
| KR | 101153383 B1 | * | 6/2012 | |
| KR | 20150043021 A | * | 4/2015 | |
| KR | 20180092771 A | * | 8/2018 | |
| KR | 102319367 B1 | | 10/2021 | |
| KR | 102329139 B1 | | 11/2021 | |
| WO | WO-2017074075 A1 | * | 5/2017 | B65G 21/10 |
| WO | WO-2018199363 A1 | * | 11/2018 | B65G 47/252 |
| WO | WO-2020004793 A1 | * | 1/2020 | B25B 11/00 |

* cited by examiner

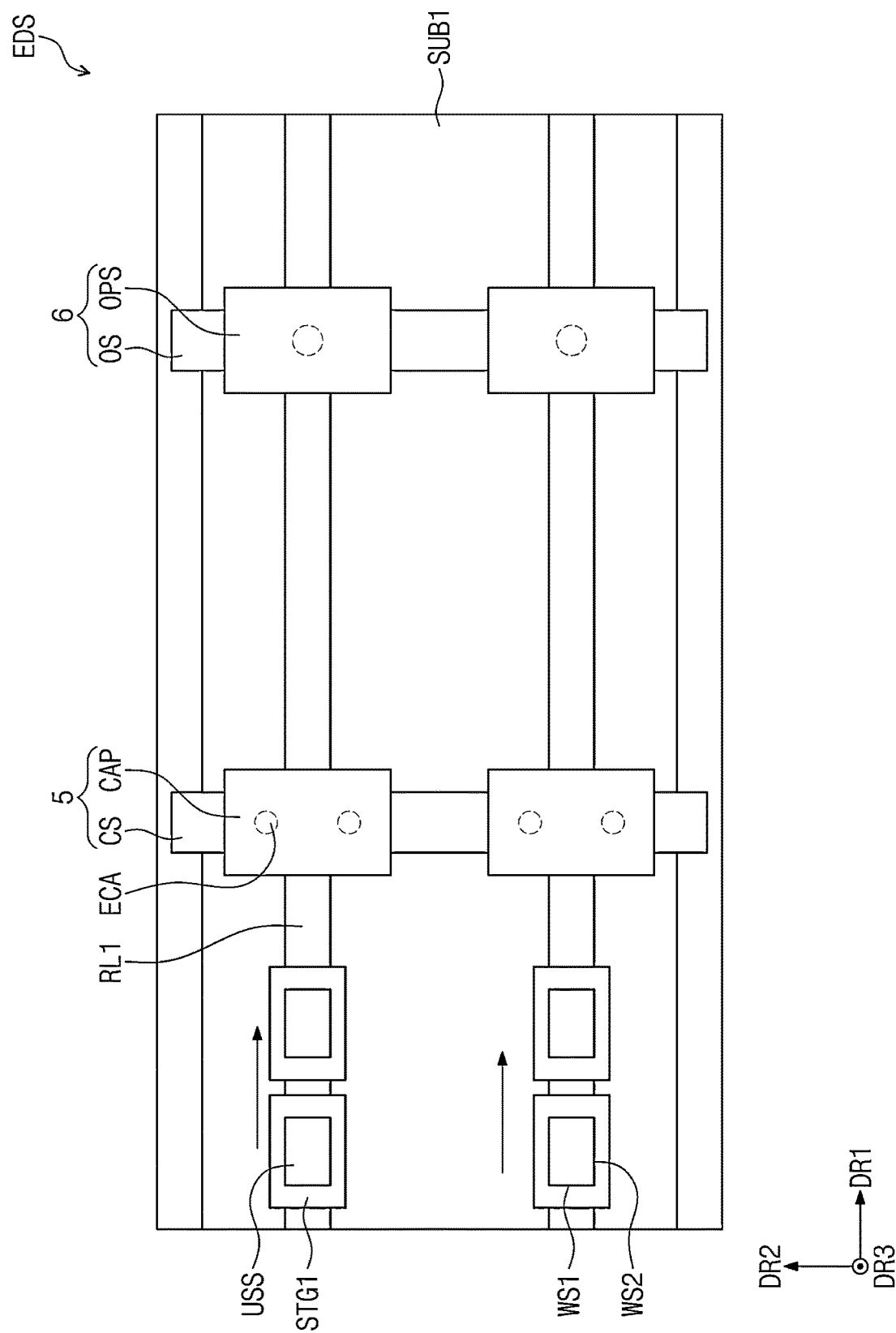

GLASS INSPECTION EQUIPMENT AND METHOD OF GLASS INSPECTION

This application claims priority to Korean Patent Application No. 10-2022-0092006, filed on Jul. 25, 2022, and all the benefits accruing therefrom under 35 U.S.C. § 119, the content of which in its entirety is herein incorporated by reference.

BACKGROUND

1. Field

Embodiments of the invention relate to a glass inspection equipment.

2. Description of the Related Art

Various display devices used in multimedia apparatuses such as televisions, mobile phones, tablet computers, and game machines have been developed. The display device includes a display panel for displaying an image and a window disposed on the display panel to protect the display panel. To reduce weight of the display device for user convenience, a thickness of the display panel is typically desired to be thin, and a thickness of the window covering the display panel becomes thinner.

SUMMARY

In a manufacturing process of a display device including a display panel and a window, a glass inspection process may be performed for examining whether a glass is defective or not. As a thickness of a glass used as the window of the display device becomes thin, the glass may be damaged during the glass inspection process. Therefore, an inspection equipment for reducing probability of the glass damage is desired.

An embodiment of the invention provides a glass inspection equipment capable of reducing probability of glass damage.

A glass inspection equipment according to an embodiment of the invention includes a first transfer rail extending in a first direction, where a glass including first sides and second sides extending in a direction intersecting the first sides reciprocates in the first direction along the first transfer rail, a rotation part disposed on the first transfer rail, where the rotation part rotates the glass, an edge inspection part disposed on the first transfer rail, where the edge inspection part inspects the first and second sides of the glass, and a surface inspection part which inspects a surface of the glass after an inspection of the first and second sides by the edge inspection part. In such an embodiment, the edge inspection part inspects the first sides when the glass in a state where the first sides thereof are arranged parallel to the first direction is transferred under the edge inspection part, and the edge inspection part inspects the second sides when the glass transferred through the edge inspection part to inspect the first side is rotated by the rotation part and the glass in a state where the second sides thereof are arranged parallel to the first direction is transferred under the edge inspection part.

A method of inspecting a glass according to an embodiment of the invention includes disposing a glass including first sides and second sides extending in a direction intersecting the first sides, on a first transfer rail to allow the glass to reciprocate in a first direction along the first transfer rail, inspecting the first and second sides using an edge inspection part when the glass is disposed under the edge inspection part disposed on the first transfer rail, inspecting a surface of the glass using a surface inspection part after the inspecting the first and second sides, and inspecting a distorted state of the glass using a distortion inspection part after the inspecting the surface of the glass. In such an embodiment, the inspecting the first sides and the second sides includes inspecting the first sides when the glass in a state where the first sides thereof are arranged parallel to the first direction and the glass is transferred under the edge inspection part, rotating the glass transferred through the edge inspection part in a way such that the second sides thereof are arranged parallel to the first direction, and inspecting the second sides when the glass in a state where the second sides thereof are arranged parallel to the first direction is transferred under the edge inspection part.

BRIEF DESCRIPTION OF THE DRAWINGS

Example embodiments will be more clearly understood from the following brief description taken in conjunction with the accompanying drawings. The accompanying drawings represent non-limiting, example embodiments as described herein.

FIGS. 7A to 7J are views illustrating an edge inspection section of a glass.

DETAILED DESCRIPTION

Figure 1A:
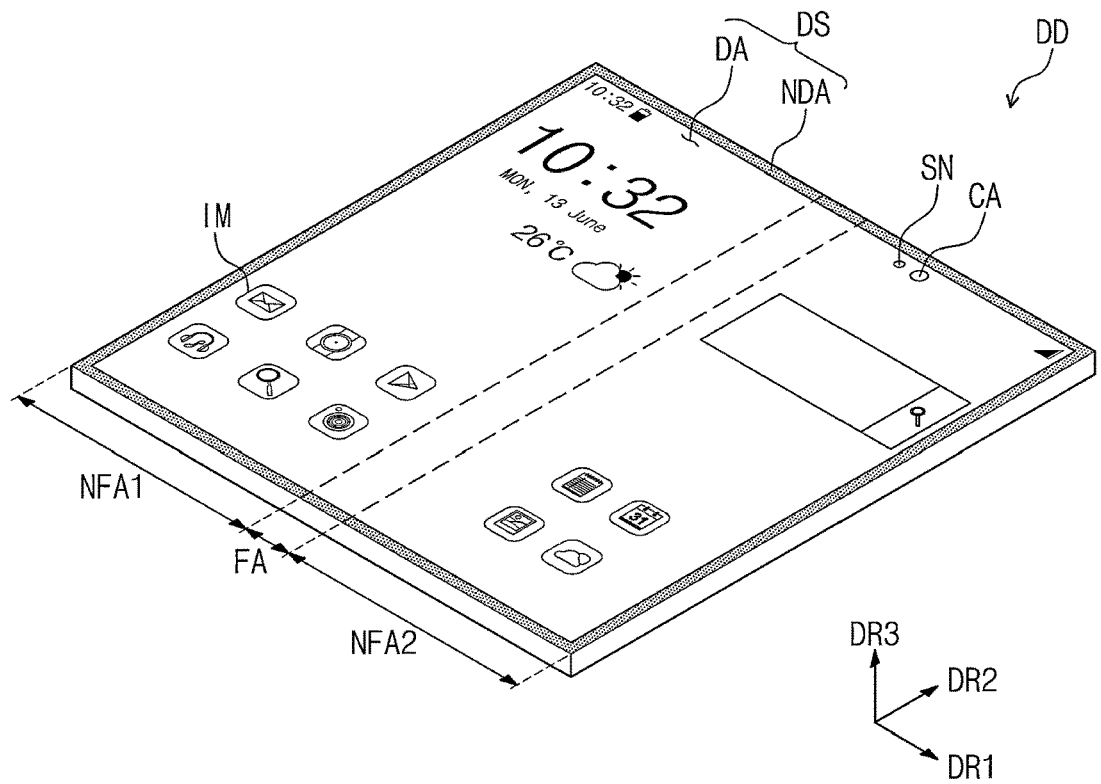
FIGS. 1A and 1B are perspective views of a display device according to an embodiment.

The invention now will be described more fully hereinafter with reference to the accompanying drawings, in which various embodiments are shown. This invention may, however, be embodied in many different forms, and should not be construed as limited to the embodiments set forth herein. Rather, these embodiments are provided so that this disclosure will be thorough and complete, and will fully convey the scope of the invention to those skilled in the art. Like reference numerals refer to like elements throughout.

When an element or a layer is referred to as being "on" another element or layer, it may be directly on the other component or intervening components may be present. In contrast, when an element or a layer is referred to as being "directly on" another element or layer, no intervening elements and/or layers are present. The term "and/or" may indicate any combination of one or more of the listed items.

Spatially relative terms, such as "below", "beneath", "lower", "above", "upper" and the like, may be used herein for ease of description to describe one element or feature's relationship to another element or feature as illustrated in the drawings. It will be understood that the spatially relative terms are intended to encompass different orientations of the device in use or operation in addition to the orientation depicted in the drawings.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings herein.

The terminology used herein is for the purpose of describing particular embodiments only and is not intended to be limiting. As used herein, "a", "an," "the," and "at least one" do not denote a limitation of quantity, and are intended to include both the singular and plural, unless the context clearly indicates otherwise. For example, "an element" has the same meaning as "at least one element," unless the context clearly indicates otherwise. "At least one" is not to be construed as limiting "a" or "an." "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Embodiments are described herein with reference to plan views and cross-sectional views that are schematic illustrations of idealized embodiments. As such, variations from the shapes of the illustrations as a result, for example, of manufacturing techniques and/or tolerances, are to be expected. Thus, embodiments should not be construed as limited to the particular shapes of regions illustrated herein but are to include deviations in shapes that result, for example, from manufacturing. Therefore, regions illustrated in the drawings are schematic in nature, and their shapes are not intended to limit the inventions but only to illustrate characteristic forms of regions of devices.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

Hereinafter, embodiments of the invention will be described in detail with reference to the accompanying drawings.

Figure 1B:
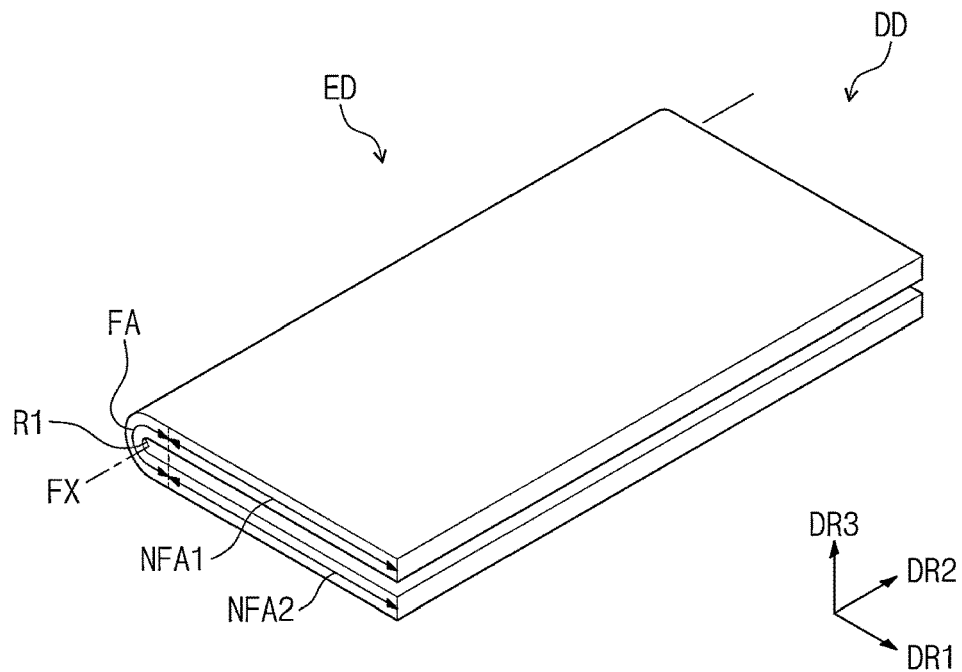

FIGS. 1A and 1B are perspective views of a display device according to an embodiment.

Referring to FIG. 1A, a display device DD according to an embodiment may have a rectangular shape having short sides extending in a first direction DR1 and long sides extending in a second direction DR2 crossing the first direction DR1. However, the invention is not limited thereto, and in an alternative embodiment, the display device DD may have various shapes, such as a circular shape and a polygonal shape. The display device DD may be a flexible display device.

Hereinafter, a direction substantially perpendicular to a plane defined by the first direction DR1 and the second direction DR2 is defined as the third direction DR3. The third direction DR3 may be a thickness direction of the display device DD. Also, in the specification, "viewed on a plane" may be defined as a state viewed in the third direction DR3.

The display device DD may include a folding area FA and a plurality of non-folding areas NFA1 and NFA2. The non-folding areas NFA1 and NFA2 may include a first non-folding area NFA1 and a second non-folding area NFA2. The folding area FA may be disposed between the first non-folding area NFA1 and the second non-folding area NFA2. The folding area FA, the first non-folding area NFA1, and the second non-folding area NFA2 may be arranged in the first direction DR1.

In an embodiment, for example, the display device DD may include a single folding area FA and two non-folding areas NFA1 and NFA2, as illustrated in FIGS. 1A and 1B, but the number of the folding area FA and the non-folding areas NFA1 and NFA2 is not limited thereto. In an alternative embodiment, for example, the display device DD may include more than two non-folding areas and a plurality of folding areas disposed between the non-folding areas.

An upper surface of the display device DD may be defined as a display surface DS, and the display surface DS may be a planar surface defined by the first direction DR1 and the second direction DR2. Images IM generated from the display device DD may be provided to a user through the display surface DS.

The display surface DS may include a display area DA and a non-display area NDA around the display area DA. The display area DA may display an image, and the non-display area NDA may not display an image. The non-display area NDA may surround the display area DA and define a border of the display device DD having or printed in a certain color.

The display device DD may include at least one sensor SN and at least one camera CA. The sensor SN and the camera CA may be adjacent to an edge of the display device DD. The sensor SN and the camera CA may be disposed in the display area DA adjacent to the non-display area NDA. The sensor SN and the camera CA may be disposed in the second non-folding areas NFA2, but the invention is not limited thereto, and in an alternative embodiment, the sensor SN and the camera CA may be disposed in the first non-folding areas NFA1.

Light may be transmitted through portions of the display device DD in which the sensor SN and the camera CA are disposed, and may be provided to the camera CA and the sensor SN. In an embodiment, the sensor SN may be an optical proximity sensor, but the type of the sensor SN is not limited thereto. The camera CA may capture an external image. In an embodiment, a plurality of sensors SN and cameras CA may be provided.

Referring to FIG. 1B, the display device DD may be a foldable display device DD capable of being folded or unfolded. In an embodiment, for example, the folding area FA may be bent based on a folding axis FX parallel to the second direction DR2, and thus the display device DD may be folded. The folding axis FX may be defined as a long axis parallel to a long side of the display device DD.

When the display device DD is folded, the first non-folding area NFA1 and the second non-folding area NFA2 may face each other, and the display device DD may be in-folded such that the display surface DS is not exposed to the outside. However, embodiments of the invention are not limited thereto. In an embodiment, for example, the display device DD may be out-folded such that the display surface DS is exposed to the outside based on the folding axis FX.

Figure 2A:
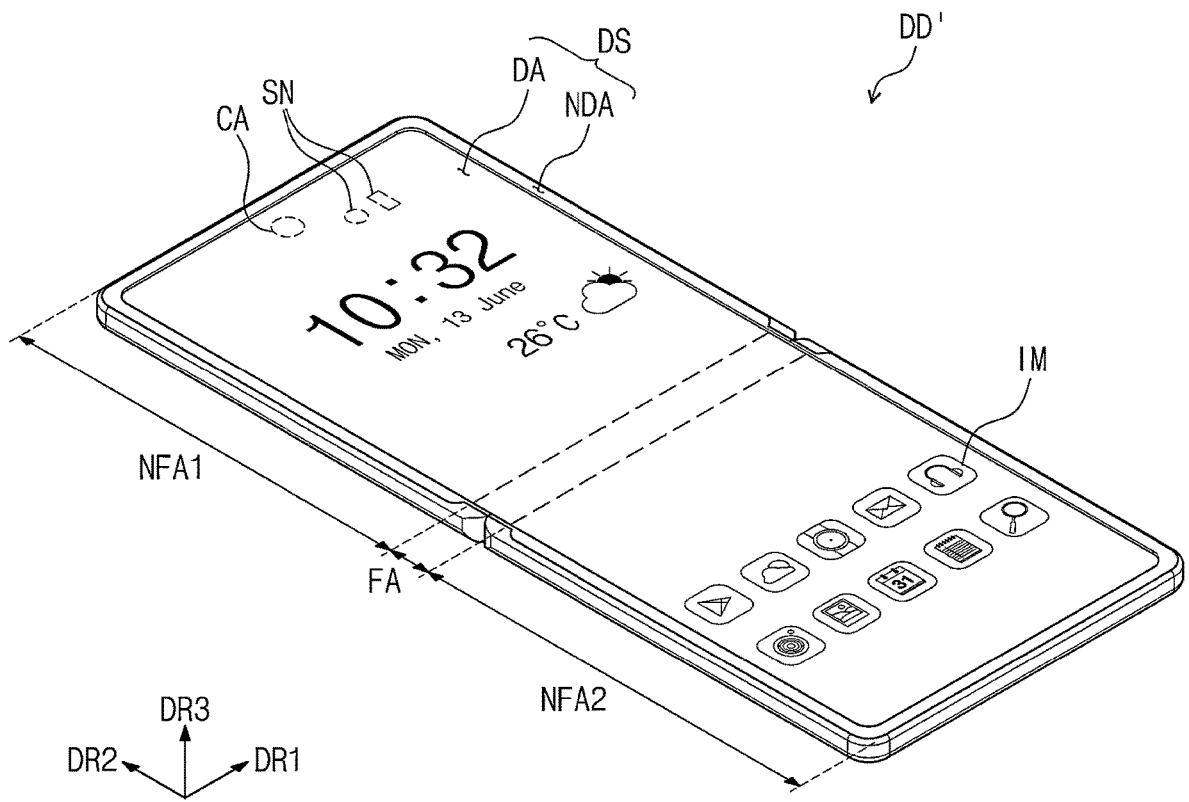
FIGS. 2A and 2B are perspective views of a display device according to an alternative embodiment.
Figure 2B:
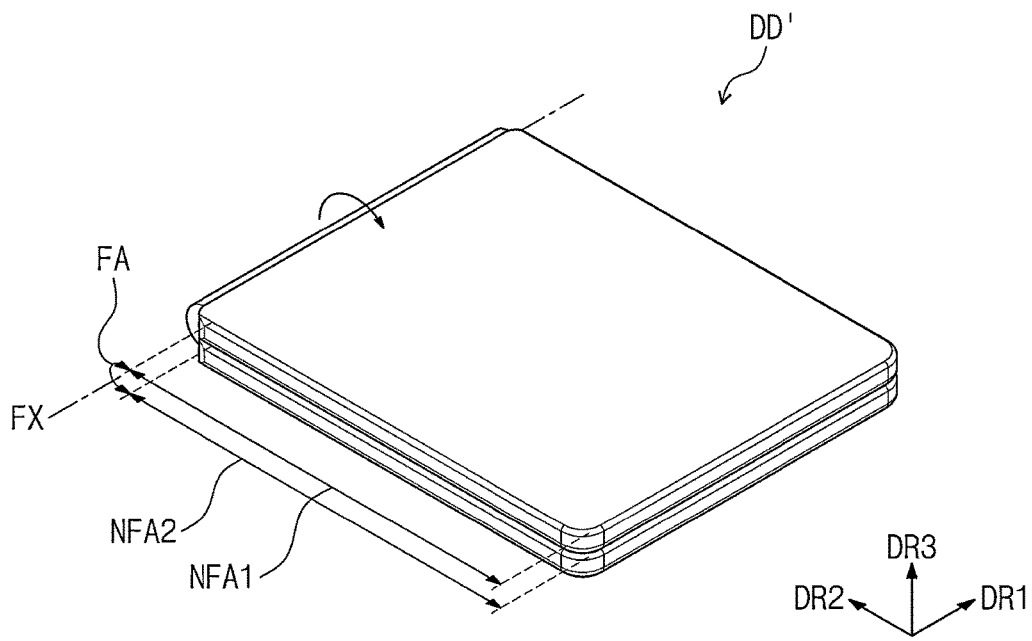

FIGS. 2A and 2B are perspective views of a display device according to an alternative embodiment.

In an embodiment of FIGS. 2A and 2B, a display area DA, a non-display area NDA, a sensor SN, and a camera CA are the same as the display area DA, the non-display area NDA, and the sensor SN, and the camera CA of FIGS. 1A and 1B described above, a description will be focused on differences from FIGS. 1A and 1B.

Referring to FIG. 2A, a display device DD' according to an embodiment may have a rectangular shape having short sides extending in a first direction DR1 and long sides extending in a second direction DR2.

A first non-folding area NFA1, a folding area FA, and a second non-folding area NFA2 may be arranged in the second direction DR2. The folding area FA may be disposed between the first non-folding area NFA1 and the second non-folding area NFA2.

Referring to FIG. 2B, the display device DD' may be a foldable display device DD' that is folded or unfolded. In an embodiment, for example, the folding area FA may be bent based on a folding axis FX parallel to the first direction DR1, and thus the display device DD' may be folded. The folding axis FX may be defined as a short axis parallel to the short side of the display device DD'.

Figure 3:
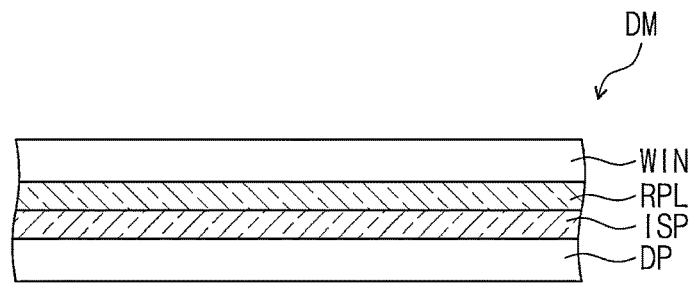
FIG. 3 is a cross-sectional view illustrating a display module.
Figure 3:
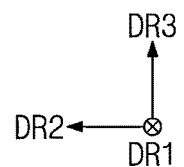

FIG. 3 is a cross-sectional view illustrating a display module.

Although not illustrated in FIGS. 1A to 2B, a display module DM of FIG. 3 may be included in embodiments of the display device DD and DD' of FIGS. 1A to 2B.

Referring to FIG. 3, in an embodiment, the display module DM may include a display panel DP, an input sensing part ISP, an anti-reflection layer RPL, and a window WIN.

The display panel DP may be a flexible display panel. The display panel DP according to an embodiment may be a light emitting display panel, and is not particularly limited. In an embodiment, for example, the display panel DP may be an organic light emitting display panel or an inorganic light emitting display panel. A light-emitting layer of the organic light emitting display panel may include an organic light-emitting material. A light-emitting layer of the inorganic light emitting display panel may include quantum dots and quantum rods. Hereinafter, for convenience of description, embodiments where the display panel DP is an organic light emitting display panel will be described in detail.

The input sensing part ISP may be disposed on the display panel DP. The input sensing part ISP may include a plurality of sensors (not shown) for sensing an external input in a capacitive manner. The input sensing part ISP may be directly formed on the display panel DP when the display module DM is formed. However, the invention is not limited thereto, and alternatively, the input sensing part ISP may be formed as a separate panel from the display panel DP, and may be attached to the display panel DP by an adhesive layer.

The anti-reflection layer RPL may be disposed on the input sensing part ISP. The anti-reflection layer RPL may be directly formed on the input sensing part ISP or may be coupled to the input sensing part ISP by an adhesive layer. The anti-reflection layer RPL may be defined as an external light anti-reflection film. The anti-reflection layer RPL may reduce reflectance of external light incident from a top of the display device DD toward the display panel DP.

When the external light incident toward the display panel DP is reflected by the display panel DP and provided to an external user again, the user may visually recognize the external light, like a mirror. To prevent this phenomenon, for example, the anti-reflection layer RPL may include a plurality of color filters for displaying same colors as the pixels of the display panel DP.

The color filters may filter external light to the same colors as the pixels. In this case, external light may not be recognized by the user. However, the invention is not limited thereto, and the anti-reflection layer RPL may include a polarizing film for reducing reflectance of external light. The polarizing film may include a retarder and/or a polarizer.

The window WIN may be disposed on the anti-reflection layer RPL. The window WIN may be directly formed on the anti-reflection layer RPL or may be coupled to the anti-reflection layer RPL by an adhesive layer. The window WIN may protect the display panel DP, the input sensing part ISP, and the anti-reflection layer RPL from external scratches and impacts.

Figure 4:
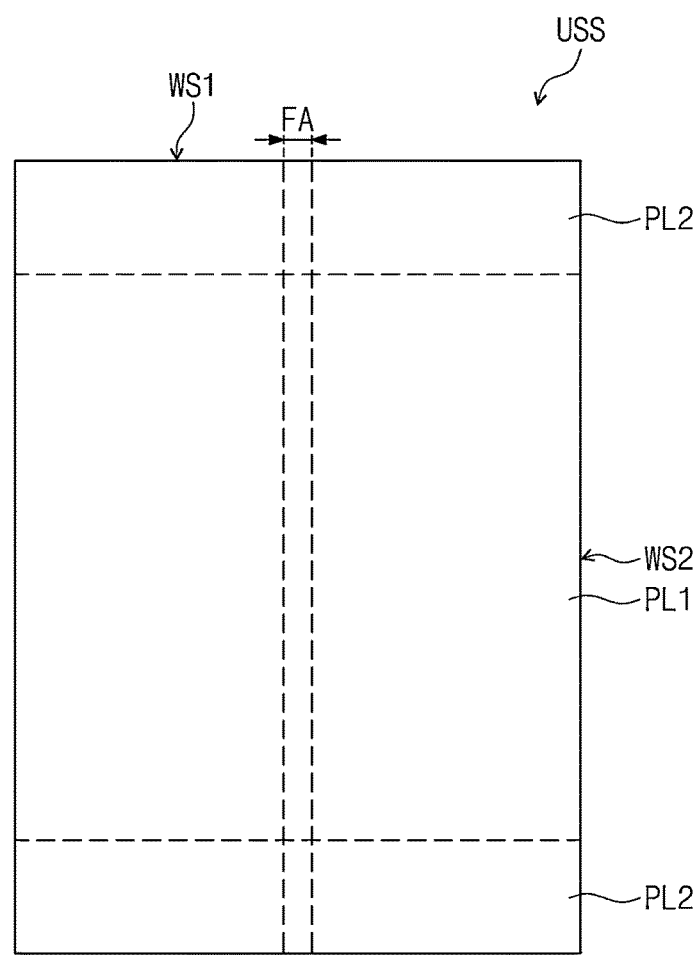
FIG. 4 is a plan view of a glass shown in FIG. 3.
Figure 4:
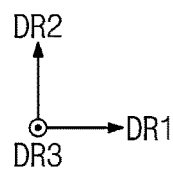

FIG. 4 is a plan view of a window shown in FIG. 3.

Hereinafter, the window WIN may be defined by a glass USS, that is, the glass USS may be used as the window WIN.

In FIG. 4, the glass USS used as the window WIN of an embodiment of the display device DD shown in FIGS. 1A and 1B is illustrated, but the invention is not limited thereto, and the glass USS may be processed differently to be used as the window WIN of an embodiment of in the display DD' in FIGS. 2A and 2B.

A folding area FA of FIG. 4 is the same as or correspond to the folding area FA of FIG. 1, and thus any repetitive detailed description thereof will be omitted.

Referring to FIG. 4, in the glass USS, sides symmetrical in a second direction DR2 and extending in a first direction DR1 and parallel to the first direction DR1 may be defined as first sides WS1. The first sides WS1 may portions overlapping (or corresponding to) the short sides of the display device DD illustrated in FIG. 1A.

Sides connected to ends of the first sides WS1, extending in the second direction DR2, and facing each other in the first direction DR1 may be defined as second sides WS2. The second sides WS2 may portions overlapping (or corresponding to) the long sides of the display device DD illustrated in FIG. 1A.

Hereinafter, the short sides refer to the first sides WS1, and the long sides refer to the second sides WS2.

The glass USS may include a first surface PL1 and second surfaces PL2 disposed above and below the first surface PL1 in the second direction DR2. The first surface PL1 may be disposed between the second surfaces PL2. A length of the first surface PL1 in the second direction DR2 may be greater than a length of each of the second surfaces PL2.

Figure 5:
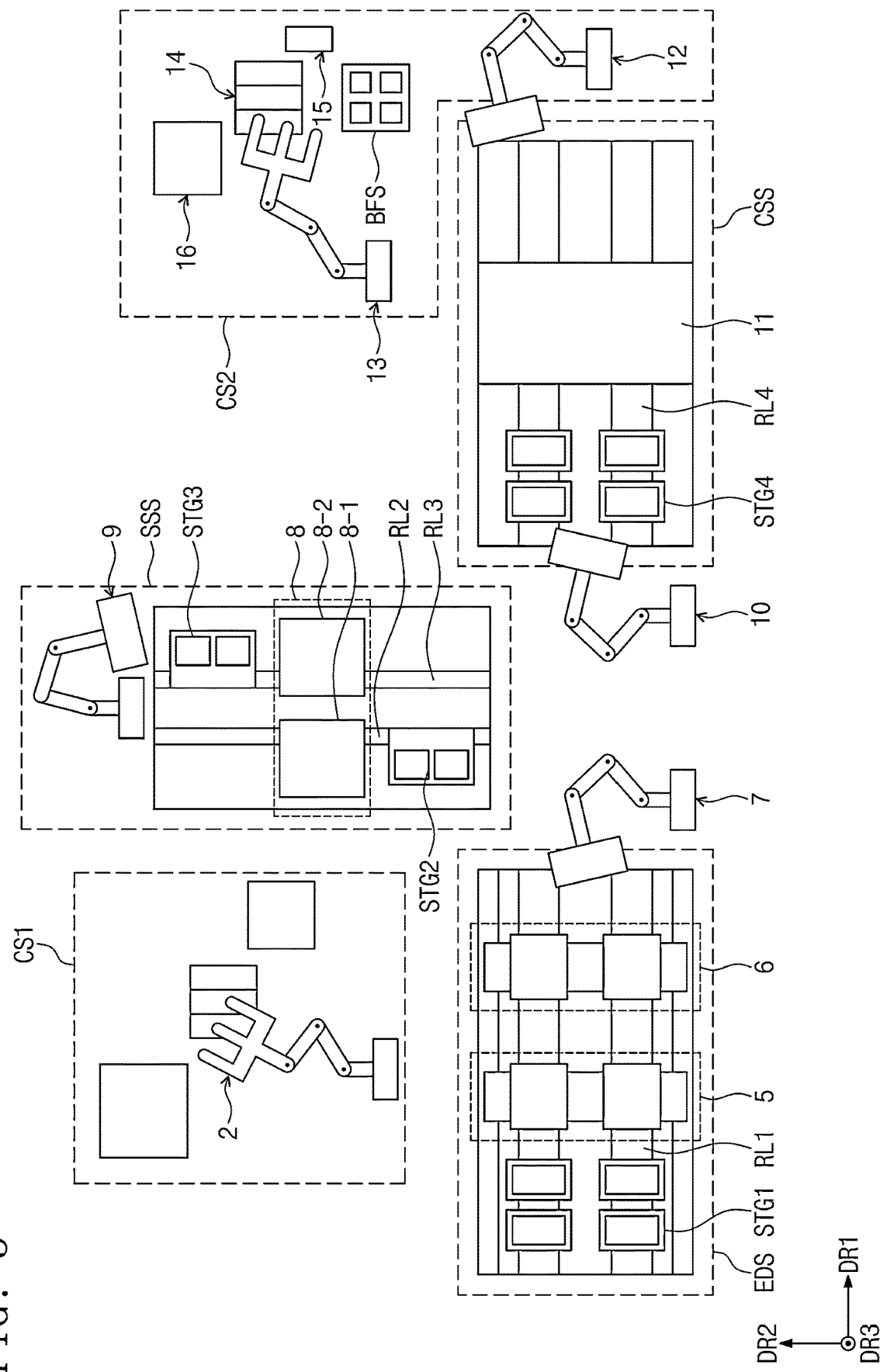
FIG. 5 is a plan view of a glass inspection equipment for inspecting a long side, a short side, a surface, and a distortion of the glass shown in FIG. 4.

FIG. 5 is a plan view of a glass inspection equipment for inspecting a long side, a short side, a surface, and a distortion of the glass shown in FIG. 4.

Referring to FIG. 5, an embodiment of a glass inspection equipment may include a first crack inspection section CS1, an edge inspection section EDS, a surface inspection section SSS, a distortion inspection section CSS, and a second crack inspection section CS2.

A crack inspection of the glass USS may be performed in the first crack inspection section CS1. The glass USS after the crack inspection may be transferred to the edge inspection section EDS by a first robot arm 2.

Edge inspection and alignment inspection of the glass USS may be performed in the edge inspection section EDS.

The glass USS where the edge inspection and the alignment inspection are completed may be transferred to the surface inspection section SSS by a second robot arm 7. In the surface inspection section SSS, presence or absence of a scratch on the surface of the glass USS may be inspected.

The glass USS where the surface inspection is completed in the surface inspection section SSS may be transferred to the distortion inspection section CSS by a fourth robot arm 10. In the distortion inspection section CSS, presence or absence of distortion generated in the glass USS in another process may be inspected.

The glass USS after completing the distortion inspection may be loaded on a buffer stage BFS of the second crack inspection section CS2 by a fifth robot arm 12, and the loaded glass USS may be transferred by a sixth robot arm 13 to a second glass accommodation part 16 through a second crack inspection part 14.

Hereinafter, the glass inspection process will be described in detail with reference to FIGS. 6A to 10 together with FIG. 5.

Figure 6A:
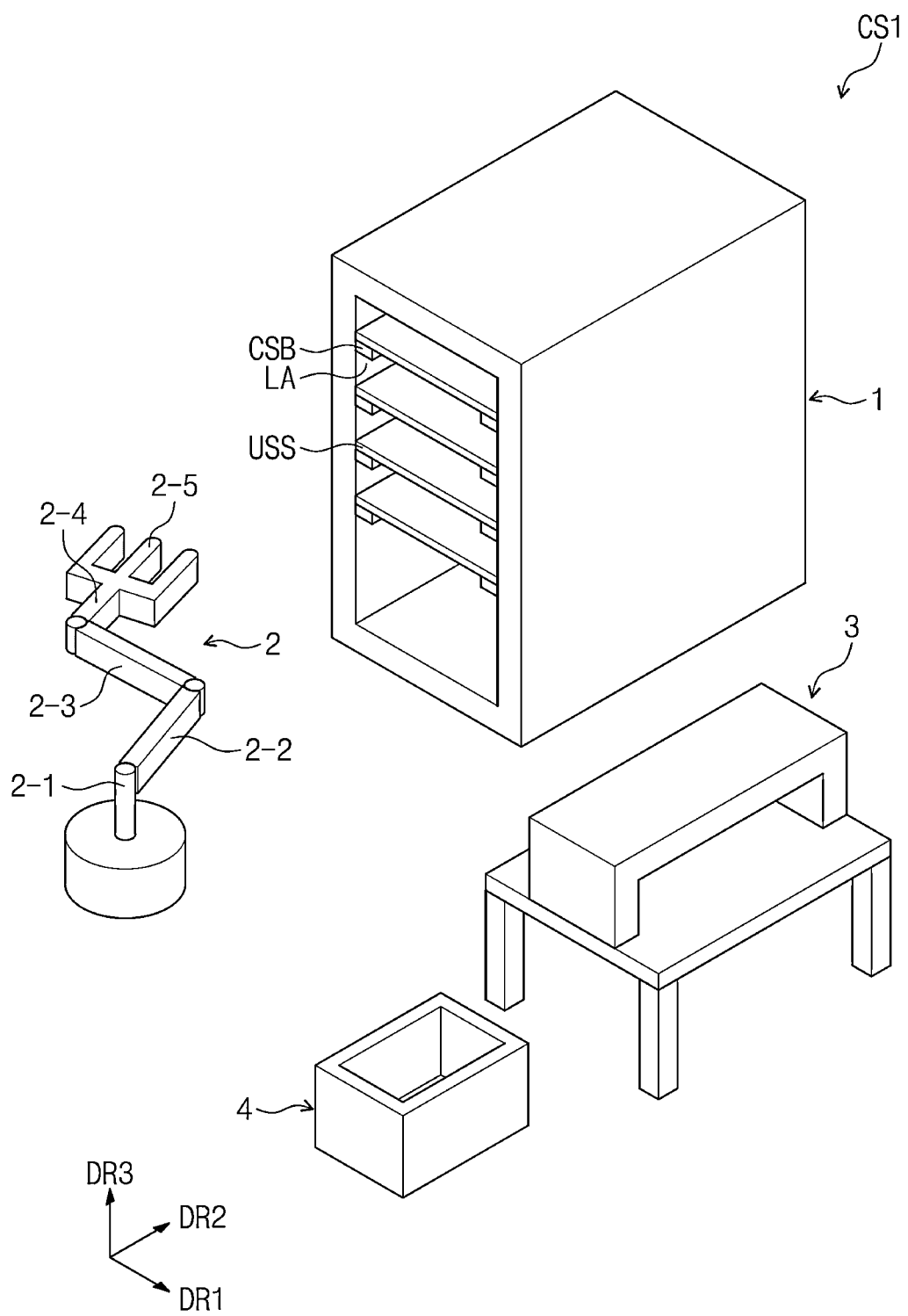
FIG. 6A is a perspective view of a first crack inspection section.
Figure 6B:
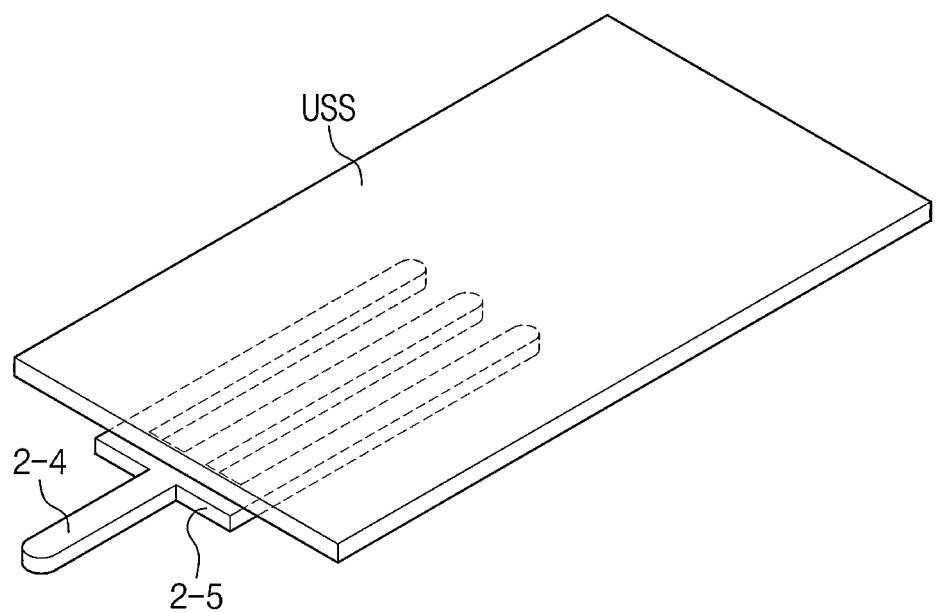
FIG. 6B is an enlarged view of fourth supports of a first robot arm of FIG. 6A.

FIG. 6A is a perspective view of a first crack inspection section shown in FIG. 5. FIG. 6B is a view illustrating a glass transferred by a first robot arm shown in FIG. 6A.

Referring to FIGS. 5, 6A and 6B, in an embodiment, the first crack inspection section CS1 includes a first glass accommodation part 1, a first robot arm 2, a first crack inspection part 3, and a first disposal part 4. The glass USS may be loaded on the first glass accommodation part 1. A shape of the first glass accommodation part 1 may be a hexahedron. However, the invention is not limited thereto, and the first glass accommodation part 1 may have various shapes.

A loading space LA for loading the glass USS may be defined on one of the surfaces of the first glass accommodation part 1 facing in the second direction DR2. The first glass accommodation part 1 may include support bars CSB disposed in the loading space LA. The pair of support bars CSB may face each other in the first direction DR1 and be disposed at a same height or level. The support bars CSB may extend in the second direction DR2 and may be arranged in the third direction DR3.

The glass USS may be disposed on the support bars CSB. The support bars CSB may support opposing sides of the glass USS. The glasses USS disposed on the support bars CSB may be arranged in the third direction DR3.

The glass USS loaded on the first glass accommodation part 1 may be transferred by the first robot arm 2. The first robot arm 2 may include a rotation shaft 2_1, a first support part 2_2, a second support part 2_3, a third support part 2_4, and a fourth support part 2_5.

One side (also referred to as a first side) of the first support part 2_2 may be connected to the rotation shaft 2_1. The other side (also referred to as a second side) of the first support part 2_2 may be connected to one side of the second support part 2_3. The first support part 2_2 may be rotated about the rotation shaft 2_1 as a central axis. Herein, the terms "one side" and "the other side" may mean opposing side portions or opposing end portions, respectively.

The other side of the second support part 2_3 may be connected to the third support part 2_4. The second support part 2_3 may be rotated about the other side of the first support part 2_2 as a central axis.

One side of the third support part 2_4 may be connected to the other side of the second support part 2_3. The third support part 2_4 may be rotated about the other side of the second support part 2_3 as a central axis. The fourth support part 2_5 may extend to the third support part 2_4.

The first robot arm 2 may transfer the glass USS loaded on the first glass accommodation part 1. In an embodiment, for example, the first robot arm 2 is drawn into the loading space LA of the first glass accommodation part 1, and as shown in FIG. 6B, the glass USS may be seated on the fourth support part 2_5. The first robot arm 2 having the glass USS seated on the fourth support part 2_5 may withdraw the glass USS from the loading space LA. In an embodiment, as shown in FIG. 6A, the glass USS seated on the fourth support part 2_5 may be provided in plural, and may be transferred by the first robot arm 2 or withdrawn from the loading space LA one by one.

The glass USS withdrawn from the loading space LA by the first robot arm 2 may be transferred to the first crack inspection part 3. The first crack inspection part 3 may inspect a crack on a surface of the glass USS. The first crack inspection part 3 may inspect the presence or absence of cracks in the glass USS by radiating light.

The first disposal part 4 may be adjacent to the first crack inspection part 3 and the first robot arm 2. When the crack exists in the glass USS, the glass USS may be disposed or discarded in the first disposal part 4. When there is no crack in the glass USS, the first robot arm 2 may transfer the glass USS onto a first transfer rail RL1 of FIG. 7A.

FIGS. 7A to 7J are views illustrating an edge inspection section of a glass.

Figure 7A:
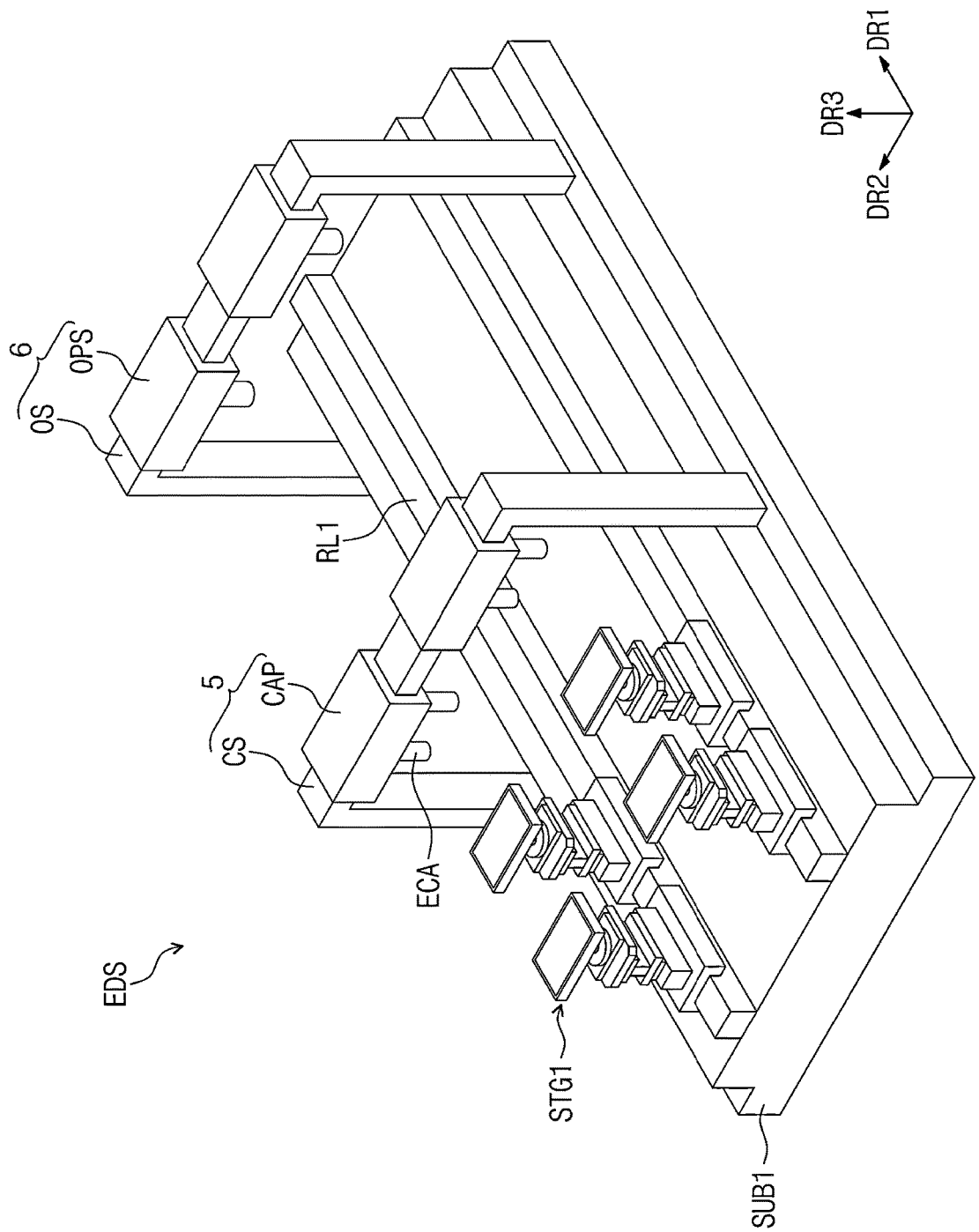
Figure 7B:
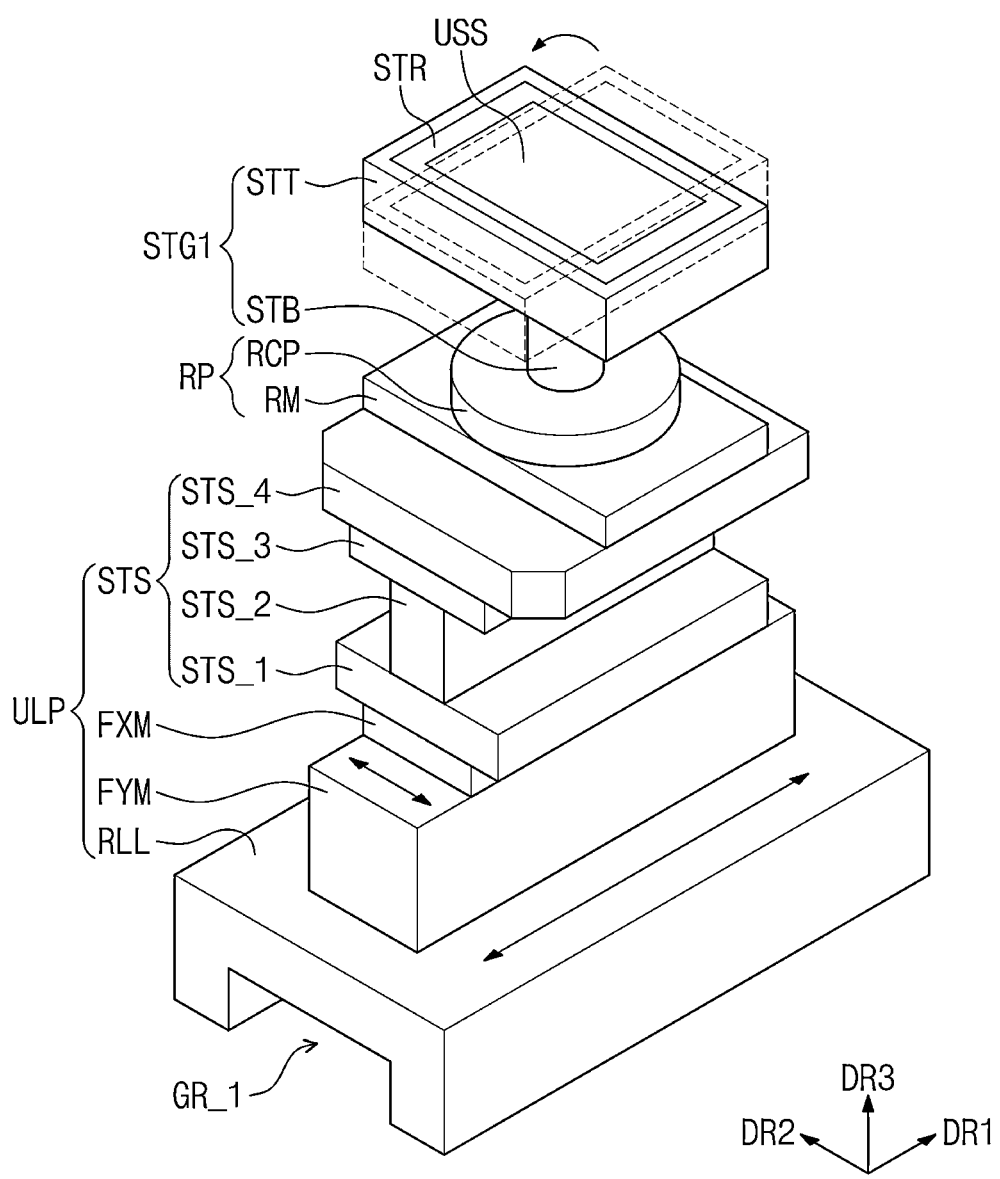

Referring to FIGS. 5, 7A, and 7B, in an embodiment, the edge inspection section EDS may include a pair of first transfer rails RL1, a pair of alignment parts ULP, a pair of rotation parts RP, a pair of first stages STG1, a pair of edge inspection parts 5, and a pair of alignment inspection parts 6. The first transfer rails RL1 may extend in the first direction DR1 and may be disposed to be spaced apart from each other in the second direction DR2.

As the inspection process performed by the components arranged on the pair of transfer rails RL1 is substantially the same as each other, only the components arranged on one of the first transfer rails RL1 will be described below.

The first transfer rail RL1, the alignment part ULP, the rotation part RP, the first stage STG1, the edge inspection part 5, and the alignment inspection part 6 may be disposed on a first lower support SUB1. The first lower support SUB1 may support the first transfer rail RL1, the alignment part ULP, the rotation part RP, the first stages STG1, the edge inspection part 5, and the alignment inspection part 6.

The alignment part ULP, the rotation part RP, the first stages STG1, the edge inspection part 5, and the alignment inspection part 6 will be described in detail below.

Referring FIGS. 7A and 7B, the alignment part ULP, the rotation parts RP, and the first stages STG1 may be disposed on the first transfer rail RL1.

Hereinafter, a configuration of the first stage STG1 and the rotation part RP will be described. The first stage STG1 may be disposed on the first transfer rail RL1, and the alignment part ULP and the rotation part RP may be disposed between the first transfer rail RL1 and the first stage STG1. The alignment part ULP may be disposed between the first transfer rail RL1 and the rotation part RP. The rotation part RP may be disposed between the first stage STG1 and the alignment part ULP. The glass USS may be disposed on the first stage STG1.

The alignment part ULP may be disposed between the first transfer rail RL1 and the rotation part RP. The alignment part ULP may include an alignment plate RLL, a left/right adjuster FYM, a front/rear adjuster FXM, and an adjustment support STS. A first rail groove GR_1 may be defined on a lower surface of the alignment plate RLL. The first transfer rail RL1 is disposed in the first rail groove GR_1. The alignment plate RLL may be disposed on the first transfer rail RL1. The alignment plate RLL may move along the first transfer rail RL1 disposed in the first rail groove GR_1.

An upper surface of the alignment plate RLL may be a planar surface defined by the first direction DR1 and the second direction DR2. The left/right adjuster FYM may be disposed on the upper surface of the planar alignment plate RLL. Hereinafter, left and right may be defined as a first direction DR1, and front and rear may be defined as a second direction DR2. The left/right adjuster FYM may reciprocate in the first direction DR1 through a motor (not shown).

The front/rear adjuster FXM may be disposed above the left/right adjuster FYM. The front/rear adjuster FXM may reciprocate in the second direction DR2 by a motor (not shown). The alignment of the glass USS may be adjusted by the left/right adjuster FYM and the front/rear adjuster FXM. Such an operation will be described below in greater detail with reference to FIG. 7H.

The adjustment support STS may be disposed on the front/rear adjuster FXM. The adjustment support STS may include a first part STS_1, a second part STS_2, a third part STS_3, and a fourth part STS_4. The second part STS_2, the third part STS_3, and the fourth part STS_4 may be disposed on the first part STS_1 in the third direction DR3.

The first part STS_1 may have a rectangular parallelepiped shape having upper and lower surfaces of a planar shape defined in the first direction DR1 and the second direction DR2. The front/rear adjuster FXM may be in contact with the lower surface of the first part STS_1. A portion of the upper surface of the first part STS_1 may be in contact with the second part STS_2.

The second part STS_2 may be disposed on the first part STS_1. The second part STS_2 may have a rectangular parallelepiped shape. A width of the second part STS_2 in the second direction DR2 may be smaller than a width of the first part STS_1, but is not limited thereto. Alternatively, a width of the second part STS_2 in the first direction DR1 may be the same as a width of the first part STS_1.

The third part STS_3 may be disposed on the second part STS_2. The third part STS_3 may have a rectangular parallelepiped shape. A width of the third part STS_3 in the second direction DR2 may be greater than a width of the second part STS_2, but is not limited thereto. Alternatively, a width of the third part STS_3 in the first direction DR1 may be the same as a width of the second part STS_2.

The fourth part STS_4 may be disposed on the third part STS_3. The fourth part STS_4 may have an octagonal pillar shape. A width of the fourth part STS_4 in the first direction DR1 and a width in the second direction DR2 may be greater than widths of the third part STS_3, respectively.

The shapes of the first part STS_1, the second part STS_2, the third part STS_3, and the fourth part STS_4 described above are merely examples, and are not limited thereto and may be variously modified.

The rotation part RP may include a rotation motor RM and a rotation disc RCP. The rotation motor RM may be disposed on a portion of an upper surface of the fourth part STS_4. Although FIG. 7B shows an embodiment where the shape of the rotation motor RM is a rectangular parallelepiped, the invention is not limited thereto and may have various shapes.

The rotation disc RCP may be disposed on an upper surface of the rotation motor RM. The shape of the rotation disc RCP may be a cylindrical shape. The rotation disc RCP may be connected to the rotation motor RM to rotate about a rotation axis parallel to the third direction DR3 on a plane defined by the first direction DR1 and the second direction DR2.

The first stage STG1 may be disposed on the rotation part RP. The first stage STG1 may include a connection bar STB and a stage part STT. The connection bar STB may have a cylindrical shape extending in the third direction DR3. Among the upper and lower surfaces of the connection bar STB opposite to each other in the third direction DR3, the lower surface may be connected to the rotation disc RCP. The upper surface of the connection bar STB may be connected to the stage part STT.

The stage part STT may be disposed on the connection bar STB. The stage part STT may have a rectangular parallelepiped shape. A seating part STR on which the glass USS is disposed may be defined on an upper surface of the stage part STT.

Figure 7C:
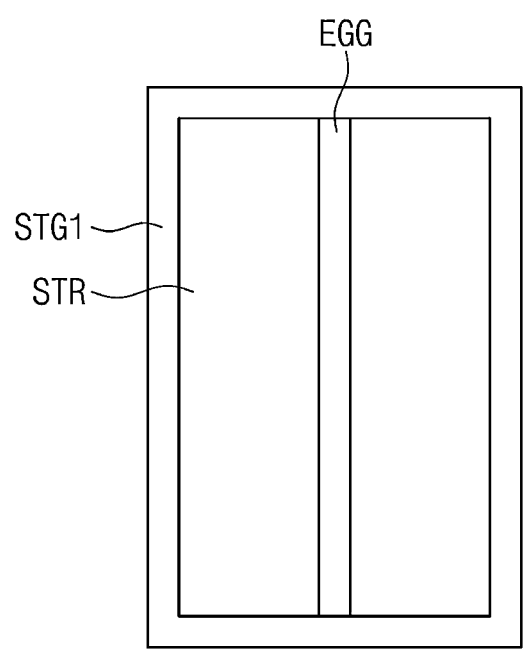

Referring to FIGS. 4 and 7C, the folding area FA extending parallel to the second direction DR2 intersecting the first direction DR1 may be defined in the glass USS, and a groove EGG overlapping the folding area FA may be defined on an upper surface of the first stage STG1. The folding area FA of the glass USS may not overlap the seating part STR of the first stage STG1 due to the groove EGG. After the glass USS is inspected, the glass USS may be used in the display device DD that is foldable by the folding axis FX as illustrated in FIGS. 1A and 1B. The glass USS may be foldable with the folding area FA of the display device DD. When the glass USS is in contact with the first stage STG1, the folding area FA of the glass USS may be damaged. In this case, when the glass USS is folded in the display device DD, the glass USS may be further damaged. In an embodiment of the invention, the groove EGG overlapping the folding area FA of the glass USS may be defined in the first stage STG1, and thus the folding area FA of the glass USS may not be in contact with the first stage STG1. Accordingly, damage to the folding area FA by the first stage STG1 may be prevented.

Referring back to FIGS. 7A and 7B, when the rotation disc RCP is rotated by the rotation motor RM, the stage part STT connected to the rotation disc RCP through the connection bar STB may rotate. As the stage part STT rotates, the glass USS disposed on the seating part STR may rotate about a rotation axis parallel to the third direction DR3.

Figure 7D:
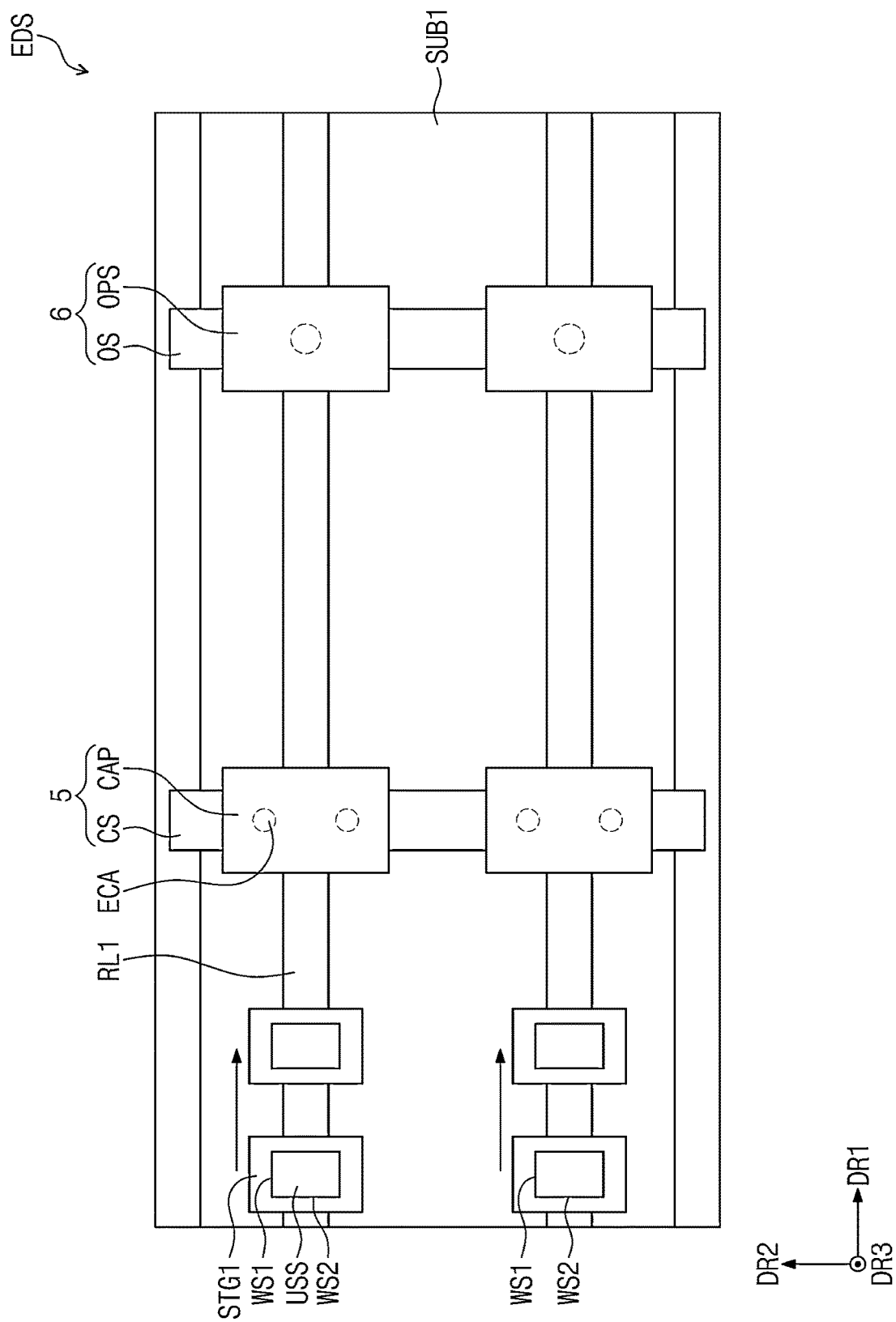
Figure 7E:
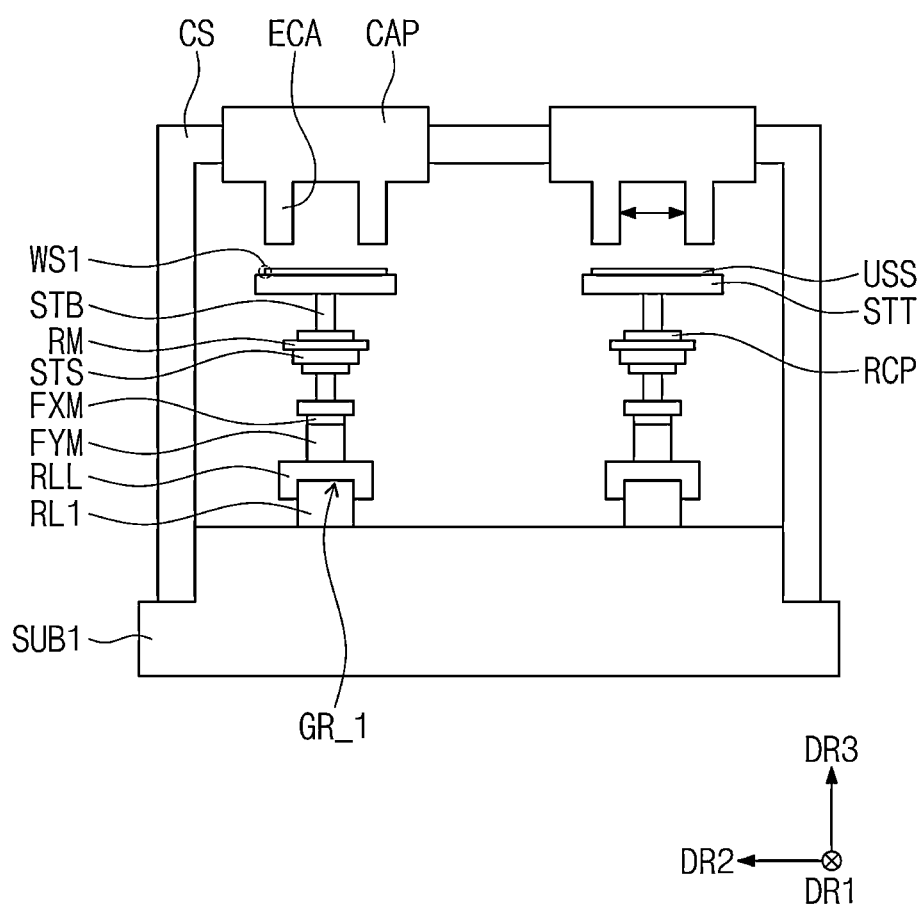

Referring to FIGS. 5, 7D, and 7E, the glass USS may be transferred in the first direction DR1 by the first transfer rail RL1 to be disposed under the edge inspection part 5. The edge inspection part 5 may include a microscope camera part CAP and a camera support CS. The camera support CS may be disposed on the first lower support SUB1 of FIG. 7A, thereby having a bridge shape. In an embodiment, for example, the camera support CS may include pillars extending in the third direction DR3 and extensions extending from upper ends of the pillars in the second direction DR2. The pillars of the camera support CS may face each other in the second direction DR2.

The microscope camera parts CAP may be disposed on the camera support CS. A plurality of microscope camera parts CAP may be provided in the second direction DR2 on the camera support CS. In an embodiment, for example, two microscope camera parts CAP may be disposed in the camera support CS. Each of the microscope camera parts CAP may include two microscope cameras ECA. In an embodiment, for example, the microscope camera ECA may be a microscope optics system. Hereinafter, a configuration of one microscope camera part CAP will be described in detail.

As the glass USS reciprocates under the edge inspection part 5 in the first direction DR1 two or more times, the first sides WS1 and the second sides WS2 may be inspected. In detail, the alignment plate RLL of FIG. 7B may move along the first transfer rail RL1, and the glass USS disposed in way such that the first sides WS1 are parallel to the first direction DR1 may be transferred in the first direction DR1. The glass USS may pass under the microscope cameras ECA. When the glass USS passes under the microscope cameras ECA, as shown in FIG. 7E, the first sides WS1 may be inspected. The microscope cameras ECA may be disposed on the first sides WS1 to inspect the first sides WS1, and thus presence or absence of cracks in the first sides WS1 may be detected.

Figure 7F:
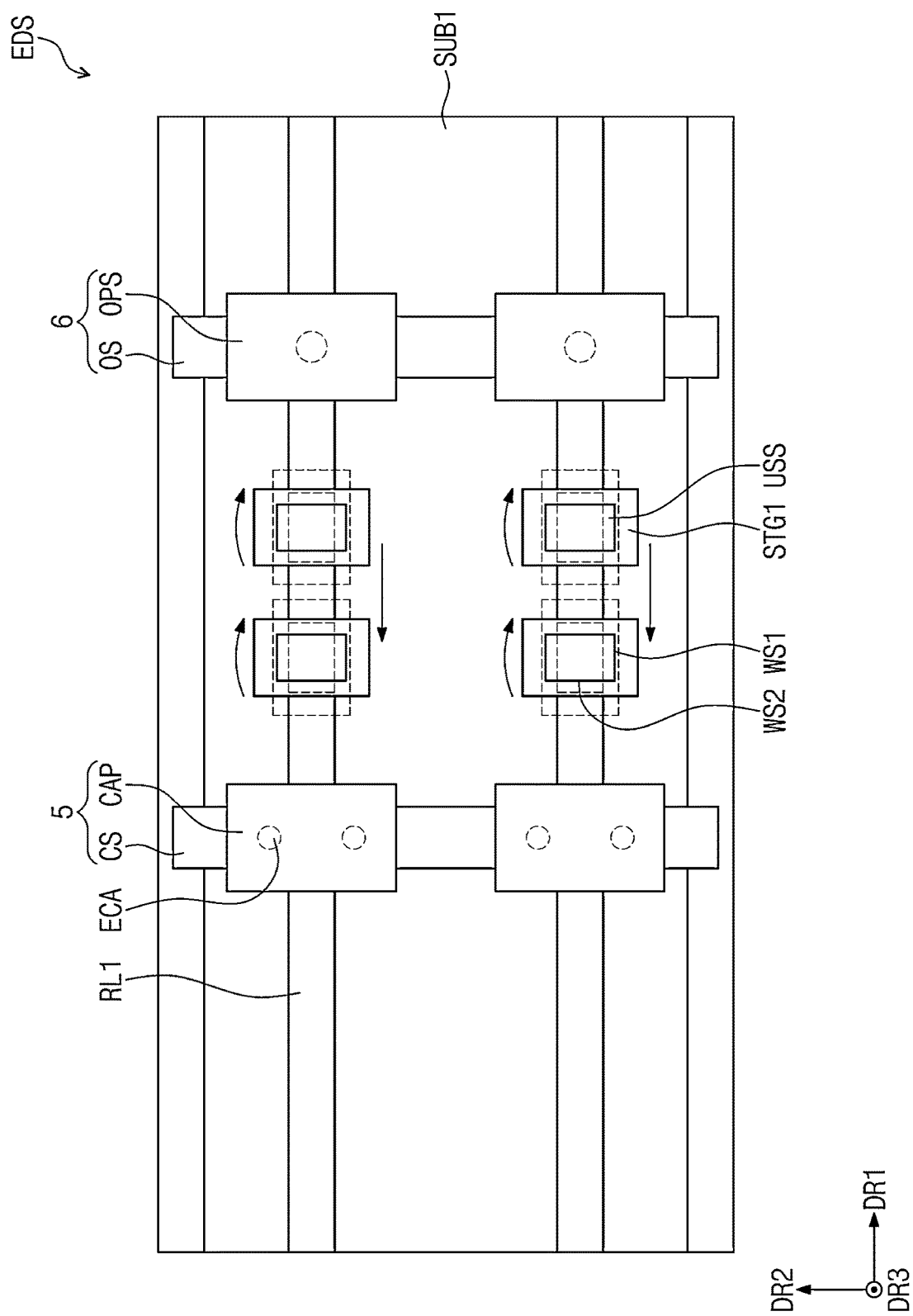

Referring to FIG. 7F, the inspected glass USS may be transferred through the edge inspection part 5. After the first stage STG1 and the glass USS are transferred through the edge inspection part 5, the first stage STG1 on which the inspected glass USS of the first sides WS1 is disposed may be rotated by 90 degrees by the rotation part RP. In an embodiment, for example, the first stage STG1 may be rotated 90 degrees in a clockwise direction. Accordingly, the second sides WS2 may be disposed to be parallel to the first direction DR1.

Referring to FIG. 7G, the alignment plate RLL disposed under the first stage STG1 rotated by 90 degrees may reciprocate in the first direction DR1 along the first transfer rail RL1. In an embodiment, for example, after the glass USS is transferred to the original position through the edge inspection part 5 again, the glass USS may be reciprocally transferred to pass the edge inspection part 5 again. When the glass USS passes under the microscope cameras ECA, the second sides WS2 may be inspected. The microscope cameras ECA may be disposed on the second sides WS2 to inspect the second sides WS2, and thus the presence or absence of cracks in the second sides WS2 may be detected.

Figure 7H:
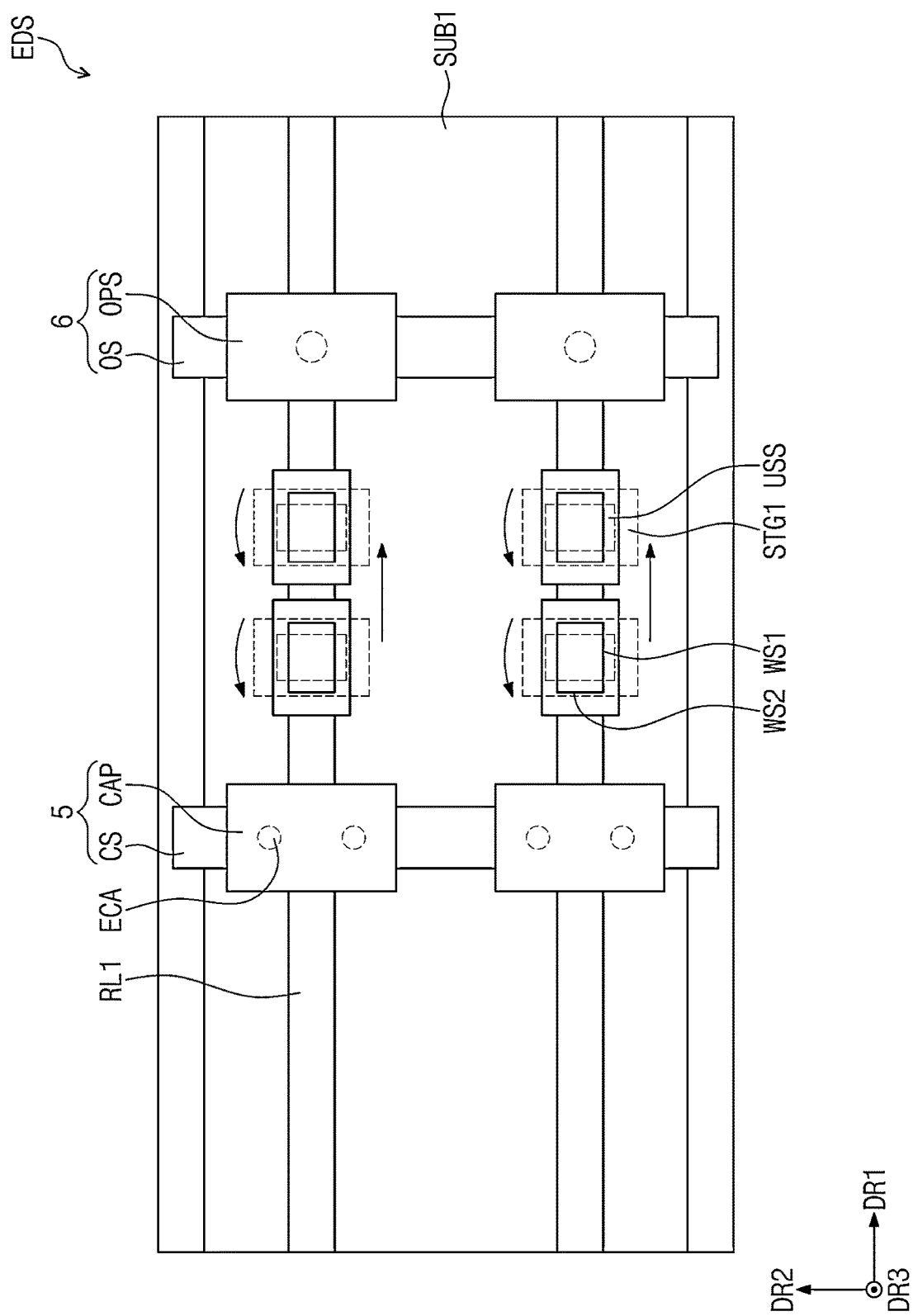

Referring to FIG. 7H, when the inspection of the first sides WS1 and the second sides WS2 is completed, the first stage STG1 passing the edge inspection part 5 again may be rotated by 90 degrees by the rotation part RP. In an embodiment, for example, the first stage STG1 may be rotated by 90 degrees counterclockwise. Accordingly, the first sides WS1 of the glass USS may be disposed parallel to the first direction DR1, and the second sides WS2 may be disposed parallel to the second direction DR2.

Conventionally, the short side inspection and the long side inspection of the glass USS may be performed through separate facilities, respectively. For example, after the short side of the glass USS is inspected, the glass USS may be transferred to another equipment to inspect the long side of the glass. An additional robotic arm may be used to transfer the glass USS. Therefore, by using the additional robot arm, the number of contact between the robot arm and the glass USS may increase, and as the number of contact increases, possibility of scratching the glass USS may be high. In an embodiment of the invention, the inspection of the short side and the long side of the glass USS is performed through rotation and reciprocation in one equipment, and thus the number of contact of the glass USS with the robot arm may not increase or be reduced. Accordingly, the possibility that scratches are formed on the glass USS may be reduced.

Figure 7I:
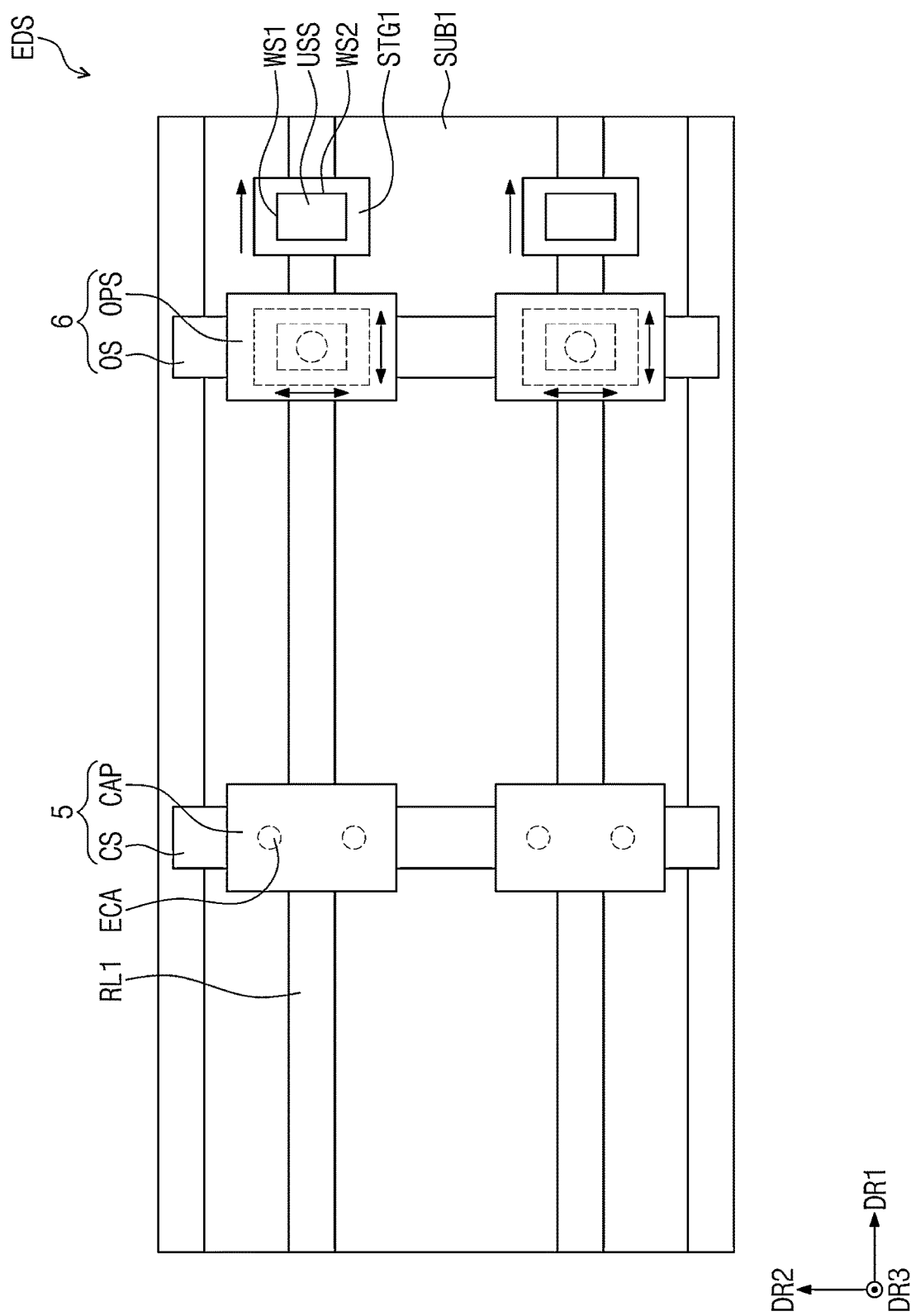

Referring to FIG. 7I, the glass USS where the inspection of the first sides WS1 and the second sides WS2 is completed may move toward the alignment inspection part 6 along the first transfer rail RL1. The alignment inspection part 6 may include an alignment inspection device OPS and a device support OS. The device support OS may be disposed on the first lower support SUB1 illustrated in FIG. 7A to have a bridge shape. In an embodiment, for example, the device support OS may include pillars extending in the third direction DR3 and extensions extending from upper ends of the pillars in the second direction DR2. The pillars of the device support OS may face each other in the second direction DR2.

The alignment inspection device OPS may be disposed on the device support OS. The plurality of alignment inspection devices OPS may be arranged in a row in the second direction DR2. In an embodiment, for example, two alignment inspection devices OPS may be disposed on the device support OS. Hereinafter, one alignment inspection device OPS will be described in detail.

The alignment state of the glass USS may be inspected while passing through the alignment inspection part 6. In an embodiment, the alignment inspection devices OPS inspect whether the glass USS is disposed at a predetermined position. When the glass USS is not disposed at the predetermined position, the alignment part ULP of FIG. 7B may align the glass USS in the first direction DR1 and the second direction DR2. The glasses USS passing through the alignment inspection part 6 may be disposed on the second stage STG2 of FIG. 8A by the second robot arm 7 of FIG. 7J.

Figure 7J:
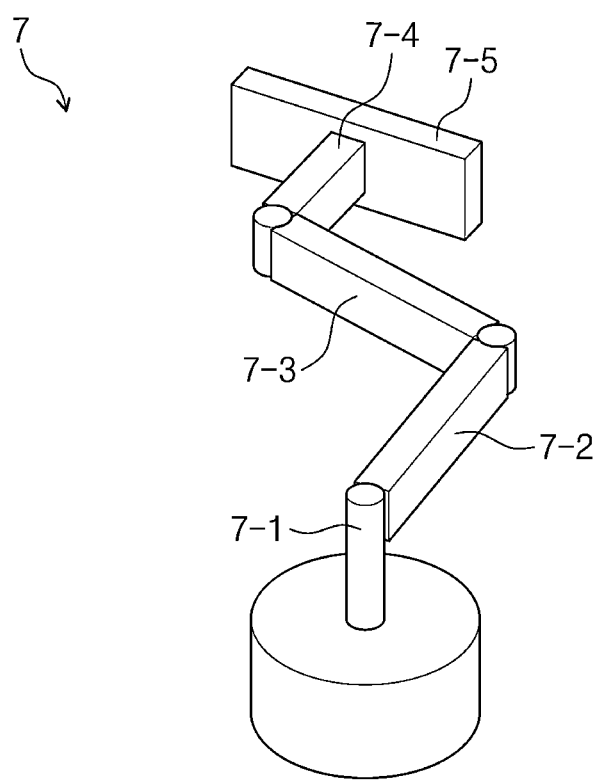

Referring to FIG. 7J, the second robot arm 7 may include a rotation shaft 7_1, a first support part 7_2, a second support part 7_3, a third support part 7_4, and a fourth support part 7_5.

The rotation shaft 7_1, the first support part 7_2, the second support part 7_3, and the third support part 7_4 of the second robot arm 7 in FIG. 7J are the same as the rotation shaft 2_1, the first support part 2_2, the second support part 2_3, and the third support part 2_4 of FIG. 6A, and thus a description thereof will be omitted.

The fourth support part 7_5 may be formed to extend from the third support part 7_4. The second robot arm 7 may transfer the glass USS in a vacuum adsorption method. In an embodiment, for example, vacuum adsorption holes (not shown) may be defined or formed on a lower surface of the fourth support part 7_5, and when the vacuum adsorption holes (not shown) are converted to a vacuum state, adsorption force may be generated on the lower surface of the fourth support part 7_5. The glass USS may be transferred by adsorbing an upper surface of the glass USS with the adsorption force.

Hereinafter, a third robot arm 9, a fourth robot arm 10, and a fifth robot arm 12 to be described later are the same as the second robot arm 7, and thus any repetitive detailed description thereof will be omitted or simplified.

FIGS. 8A to 8G are views illustrating a surface inspection section of a glass.

Since the glass USS of FIGS. 8A to 8G is the same as the glass USS of FIG. 4, any repetitive detailed description thereof will be omitted or simplified.

Figure 8A:
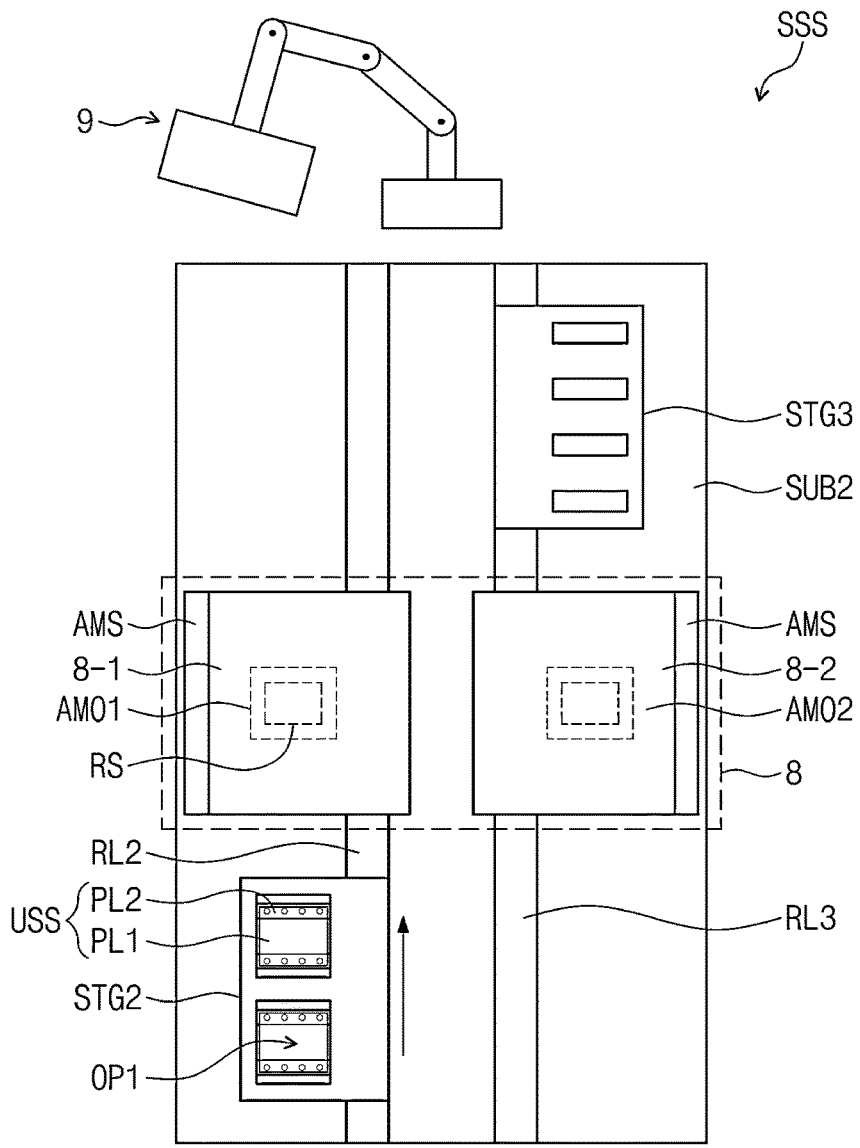
FIGS. 8A to 8G are views illustrating a surface scratch inspection section of glass.
Figure 8A:
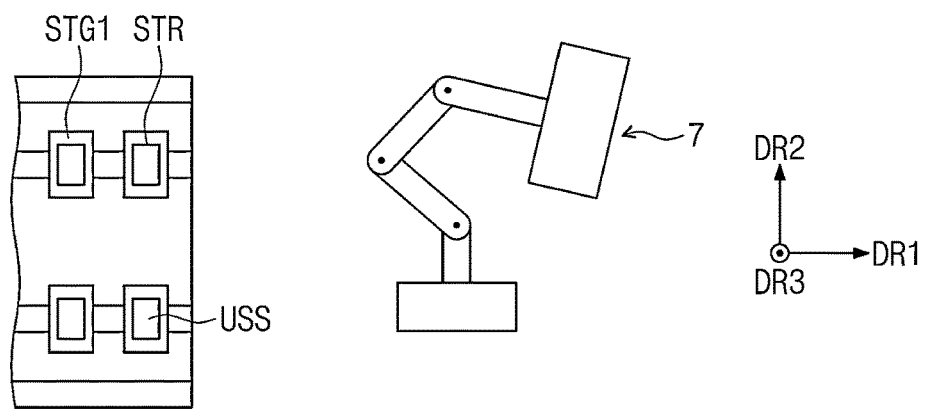

Referring to FIGS. 5 and 8A, the surface inspection section SSS may include a second lower support SUB2, an inspection part supports AMS, a second transfer rail RL2, a second stage STG2, a third transfer rail RL3, a third stage STG3, and a surface inspection part 8.

The inspection part support AMS, the second transfer rail RL2, the second stage STG2, the third transfer rail RL3, the third stage STG3, and the surface inspection part 8 may be disposed on the second lower support SUB2. The second transfer rail RL2 and the third transfer rail RL3 may extend in a second direction DR2 and may be disposed to be spaced apart from each other in a first direction DR1.

Figure 8B:
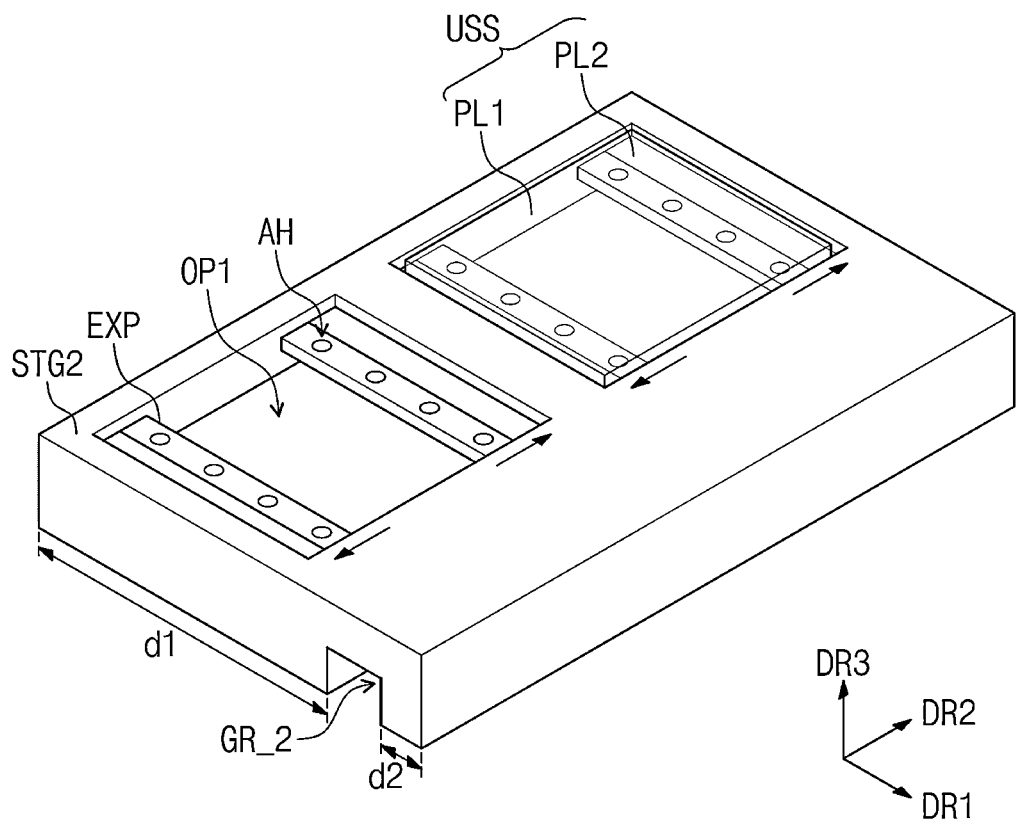

Referring to FIG. 8B, in an embodiment, the second stage STG2 may have a hexahedral shape. A second rail groove GR_2 may be defined on a lower surface of the second stage STG2. The second rail groove GR_2 may not be defined at a center of the lower surface of the second stage STG2. In an embodiment, a distance d1 between the second rail groove GR_2 and one side of the second stage based on the first direction DR1 may be greater than a distance d2 between the second rail groove GR_2 and the other side thereof. The second transfer rail RL2 may be disposed in the second rail groove GR_2. As the second transfer rail RL2 is disposed in the second rail groove GR_2, the second stage STG2 may reciprocate in the second direction DR2 along the second transfer rail RL2.

A plurality of first openings OP1 may be defined on the upper surface of the second stage STG2. Hereinafter, one opening OP1 will be described. A pair of glass extension parts EXP may be disposed to face each other in the second direction DR2 around an entrance of the first opening OP1. A plurality of adsorption holes AH may be defined on an upper surface of each of the pair of glass extension parts EXP.

A first surface PL1 of the glass USS disposed on the second stage STG2 may overlap the first opening OP1. A second surfaces PL2 may be disposed to overlap the glass extension parts EXP. The pair of glass extension parts EXP may fix the second surfaces PL2 of the glass USS through the adsorption holes AH. The pair of glass extension parts EXP may move in the second direction DR2 to be spaced apart from each other. Accordingly, the glass USS may be expanded to be flat.

Figure 8C:
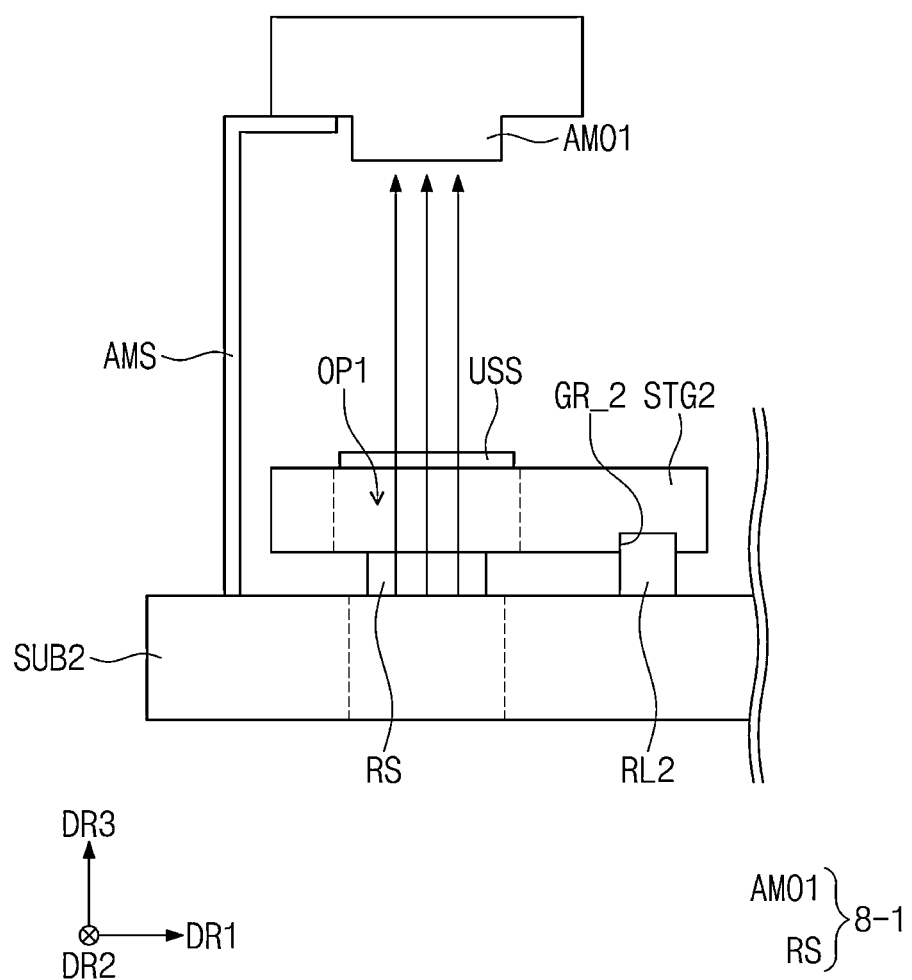

Referring to FIGS. 5, 8A, and 8C, the surface inspection part 8 may include inspection part supports AMS, a first surface inspection part 8-1, and a second surface inspection part 8-2. The inspection part supports AMS may be disposed on the second lower support SUB2 symmetrically in the first direction DR1. Hereinafter, one inspection part support AMS will be described.

The inspection part support AMS may have an inverted 'L'-like shape. In an embodiment, for example, the inspection part support AMS may include a pillar extending in the third direction DR3 and an extension extending from the upper end of the pillar in the first direction DR1.

The first surface inspection part 8-1 may include an optical system camera AMO1 and a light source RS. The light source RS may be disposed on the second lower support SUB2, and may be disposed on the same plane as the second transfer rail RL2. Light may be radiated from the light source RS.

The optical system camera AMO1 may be disposed on the extension extending in the first direction DR1 of the inspection part support AMS. The optical system camera AMO1 of the surface inspection part 8 may be, for example, a high-precision optical system camera.

Figure 8D:
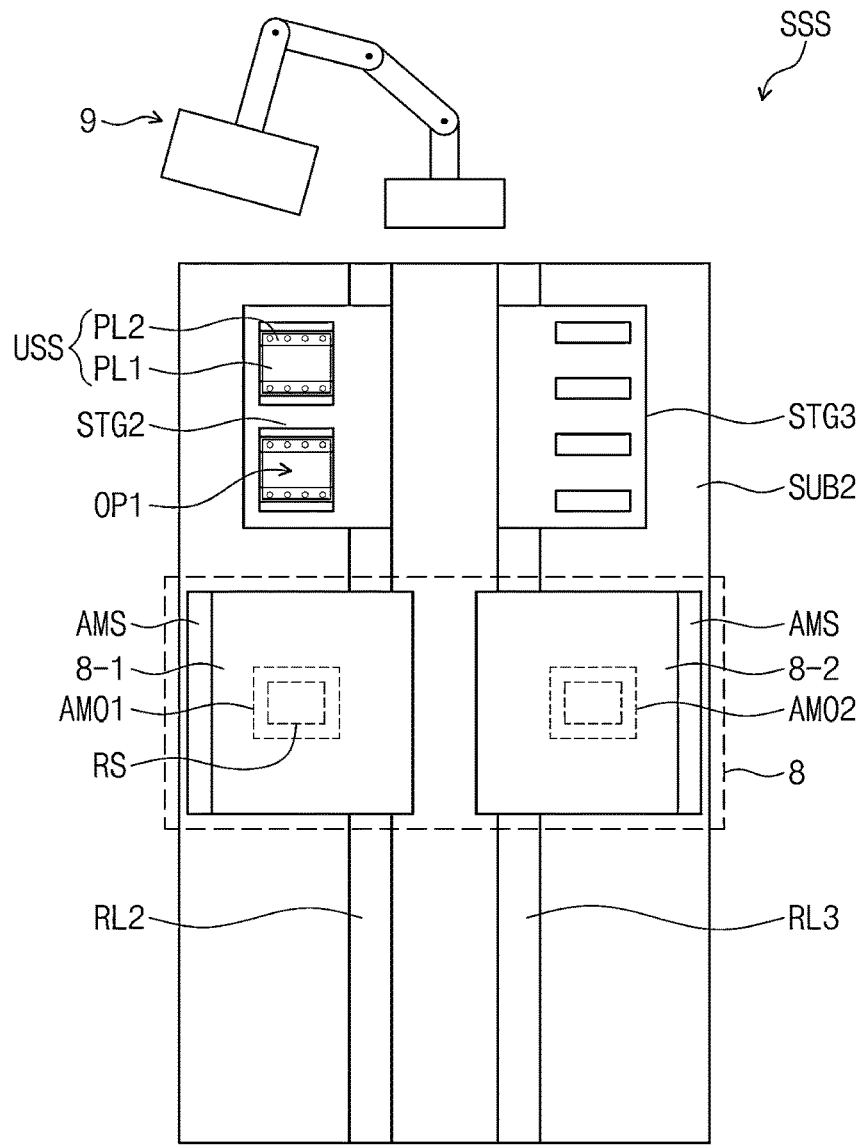
Figure 8D:
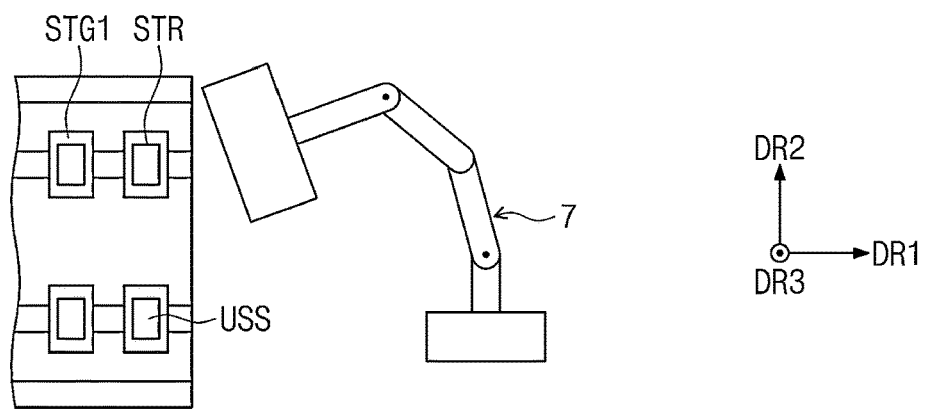

The glass USS may be transferred in the second direction DR2 by the second transfer rail RL2 to be disposed between the optical system camera AMO1 and the light source RS. When the glass USS is disposed between the optical system camera AMO1 and the light source RS, as shown in FIG. 8C, the first surface PL1 of the glass USS may be inspected. In an embodiment, when the first surface PL1 is disposed between the optical system camera AMO1 and the light source RS, light may be emitted from the light source RS. The light emitted from the light source RS and passing through the first surface PL1 may be collected (or detected) by the optical system camera AMO1. The optical system camera AMO1 may inspect scratches on the first surface PL1 with the collected light. As shown in FIG. 8D, the glasses USS where the surface inspection of the first surface PL1 is completed may pass through the first surface inspection part 8-1 and may move in the second direction DR2.

The glass USS passing through the first surface inspection part 8-1 may be transferred from the second stage STG2 to the third stage STG3 by the third robot arm 9.

Figure 8E:
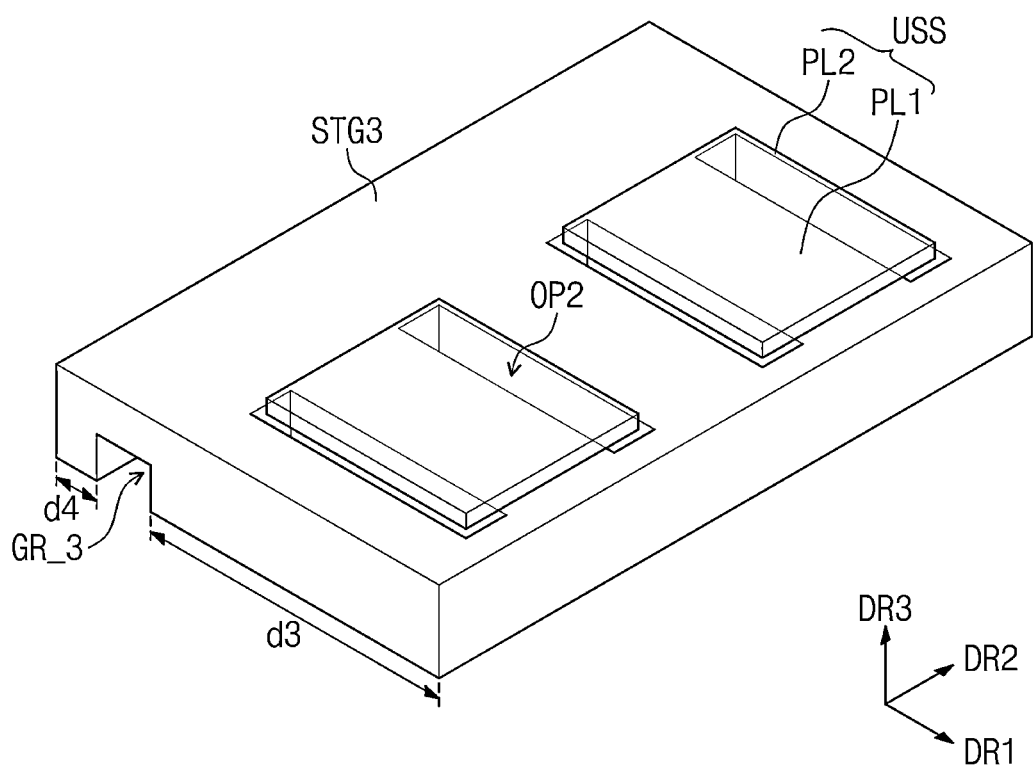

Referring to FIG. 8E, the third stage STG3 may have a hexahedral shape. A third rail groove GR_3 may be defined on a lower surface of the third stage STG3. The third rail groove GR_3 may not be defined at a center of the lower surface of the third stage STG3. In detail, a distance d3 between the third rail groove GR_3 and one side of the third stage STG3 based on the first direction DR1 may be greater that a distance d4 between the third rail groove GR_3 and the other side thereof. The third transfer rail RL3 may be disposed in the third rail groove GR_3. As the third transfer rail RL3 is disposed in the third rail groove GR_3, the third stage STG3 may reciprocate in the second direction DR2 along the third transfer rail RL3.

A plurality of second openings OP2 may be defined on an upper surface of the third stage STG3. The second openings OP2 may be arranged in the second direction DR2. Hereinafter, one second opening OP2 will be described. The second opening OP2 may have a rectangular shape extending longer in the first direction DR1 than in the second direction DR2 when viewed on a plane view.

The second surfaces PL2 of the glass USS may be disposed to overlap the second opening OP2. The first surface PL1 may be disposed to overlap a portion of the upper surface of the third stage STG3.

Figure 8F:
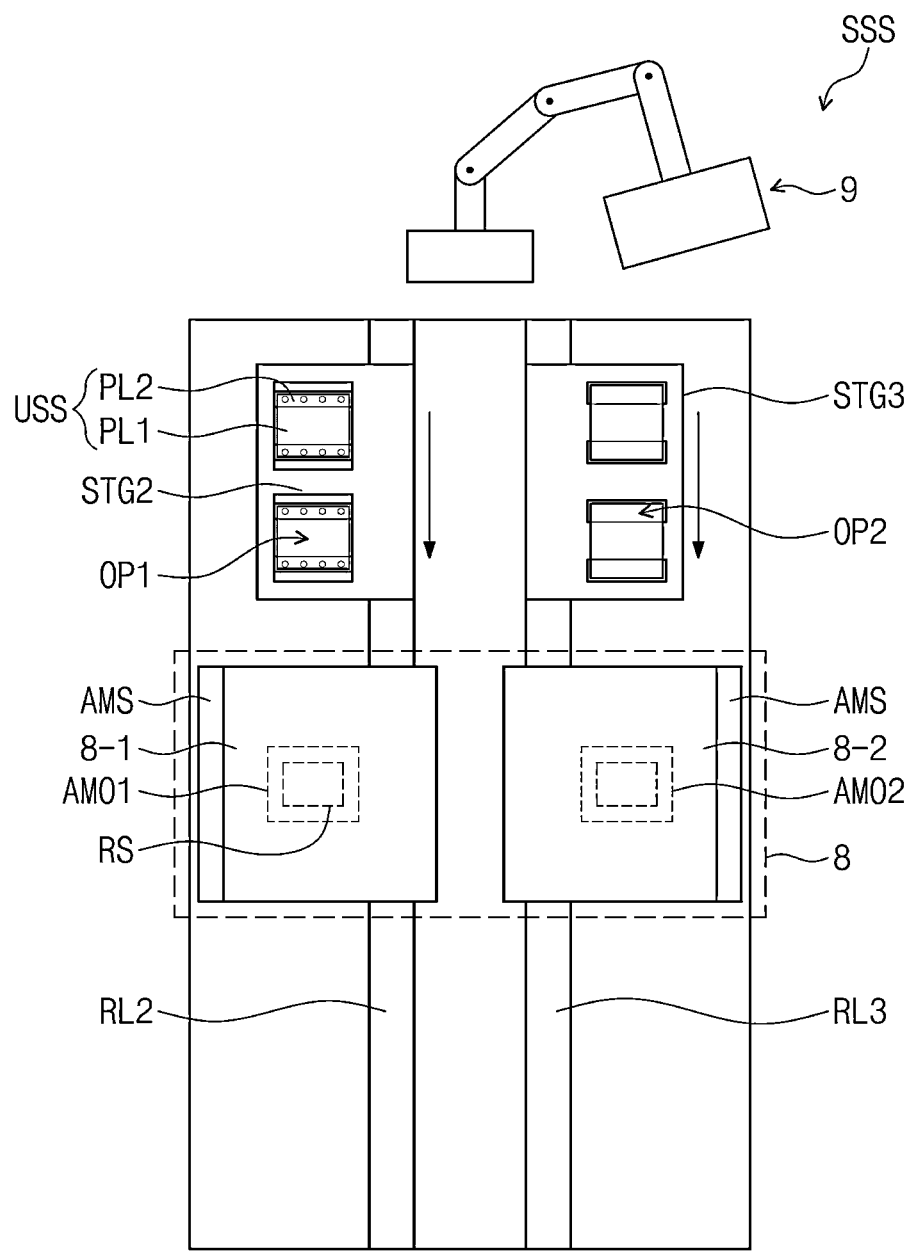
Figure 8G:
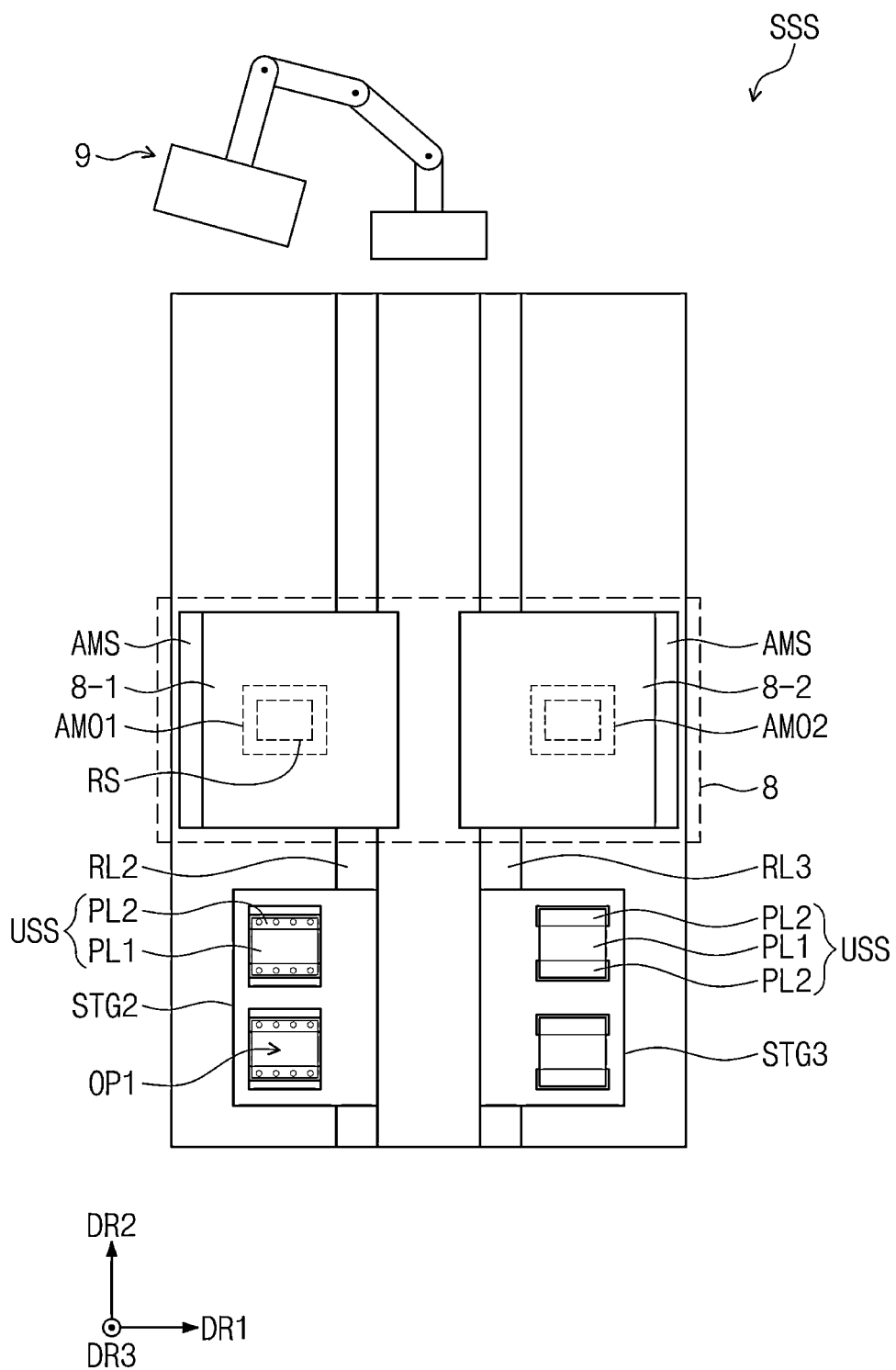

Referring to FIGS. 5, 8F, and 8G, the glasses USS disposed on the third stage STG3 may move toward the second surface inspection part 8-2 along the third transfer rail RL3. A configuration of the second surface inspection part 8-2 is the same as that of the first surface inspection part 8-1, and thus any repetitive detailed description thereof will be omitted.

When the glass USS is disposed between the light source RS and an optical system camera AMO2 of the second surface inspection part 8-2, surface scratches on the second surfaces PL2 overlapping an extension EXP in FIGS. 8A and 8B may be inspected. In an embodiment, light may be emitted from the light source RS, pass through the second surfaces PL2 of the glass USS, and then be collected (or detected) by the optical system camera AMO2. The optical system camera AMO2 may inspect the scratches on the second surfaces PL2 of the glass USS with the collected light. The glasses USS after the surface inspection of the second surfaces PL2 may pass through the second surface inspection part 8-2 and move in the second direction DR2, as shown in FIG. 8G.

FIGS. 9A to 9D are views illustrating a distortion inspection section of a glass.

Figure 9A:
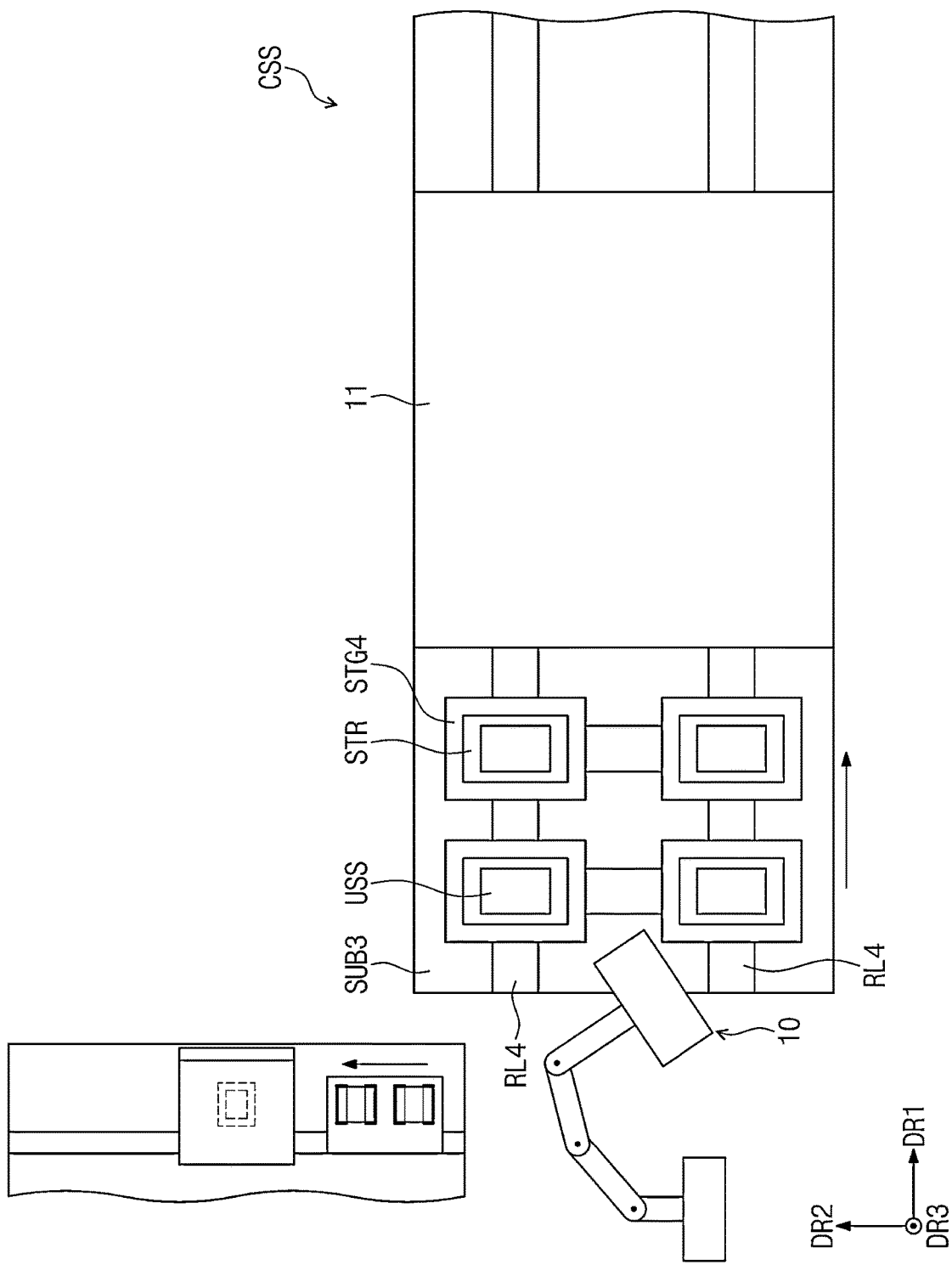
FIGS. 9A to 9D are views illustrating a distortion inspection section of a glass.

Referring to FIGS. 5 and 9A, the glasses USS where the surface inspection is completed may be transferred to a distortion inspection section CSS by the fourth robot arm 10.

The distortion inspection section CSS may include a third lower support SUB3, fourth stages STG4, fourth transfer rails RL4, and a distortion inspection part 11. The fourth stages STG4, the pair of fourth transfer rails RL4, and the distortion inspection part 11 may be disposed on a third lower support SUB3. The third lower support SUB3 may support the fourth stages STG4, the pair of fourth transfer rails RL4, and the distortion inspection part 11.

The glasses USS may be disposed on the fourth stage STG4. The fourth stage STG4 may have a hexahedral shape. A seating part STR may be defined on an upper surface of the fourth stage STG4. The seating part STR may have a rectangular shape, but is not limited thereto and may have various shapes. The glass USS may be disposed on the seating part STR.

Figure 9B:
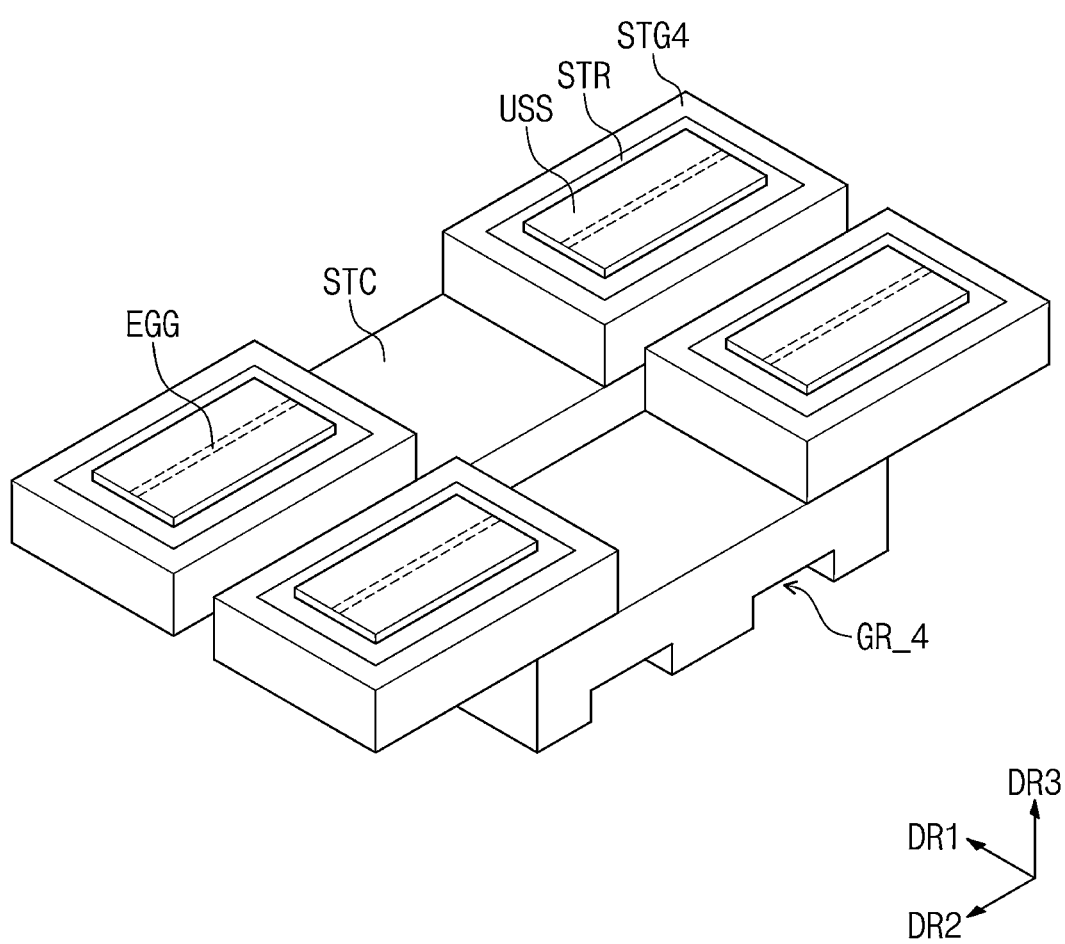

Referring to FIGS. 4, 7C, and 9B, the groove EGG described above with reference to FIG. 7C may be defined in the seating part STR defined on an upper surface of the fourth stage STG4. The folding area FA of the glass USS may overlap the groove EGG defined in the seating part STR of the fourth stage STG4. The groove EGG is substantially the same as that described above with reference to FIG. 7C, and thus any repetitive detailed description thereof will be omitted.

A stage connector STC may be disposed under the fourth stage STG4. The stage connector STC may have a rectangular parallelepiped shape. Two fourth stages STG4 may be disposed to face each other in the second direction DR2 on a portion of an upper surface of the stage connector STC. A pair of fourth rail grooves GR_4 may be defined on a lower surface of the stage connector STC. A pair of fourth transfer rails RL4 may be disposed in the pair of fourth rail grooves GR_4. The stage connector STC may reciprocate in the first direction DR1 along the pair of fourth transfer rails RL4. Accordingly, the glasses USS disposed on the fourth stage STG4 may move in the first direction DR1 toward the distortion inspection part 11.

Figure 9C:
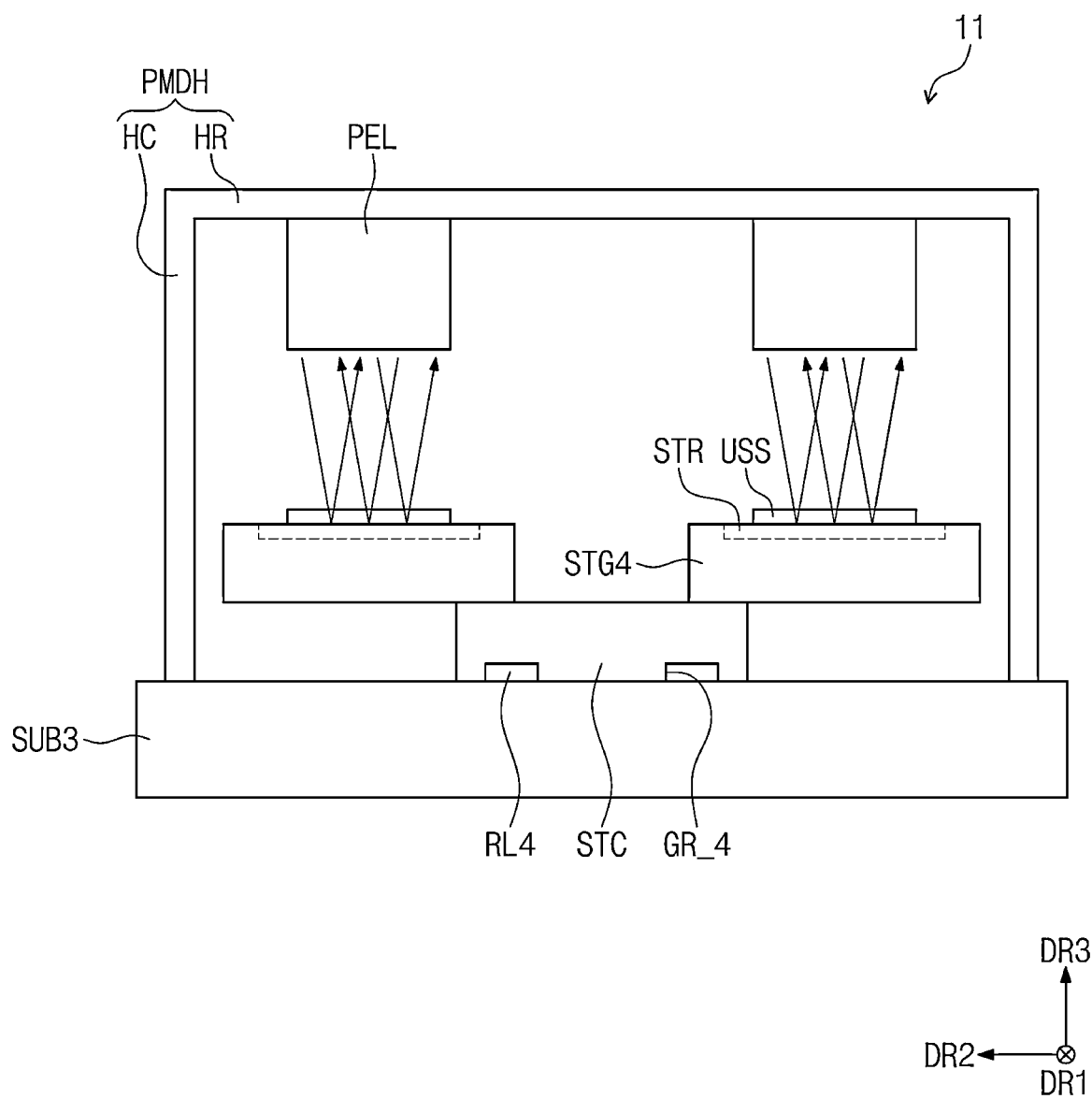

Referring to FIG. 9C, the distortion inspection part 11 may include a cover house PMDH and a refractive optical system PEL. The cover house PMDH may include pillars HC and a roof HR. Each of the pillars HC may extend in the third direction DR3. The roof HR may extend in the second direction DR2 from upper sides of the pillars HC.

A plurality of refractive optical systems PEL may be disposed on the roof HR. In an embodiment, two refractive optical systems PEL may be provided in the cover house PMDH. Hereinafter, one refractive optical system PEL will be described.

When the glass USS moves in the first direction DR1 along the pair of fourth transfer rails RL4 and is disposed under the refractive optical system PEL, the refractive optical system PEL may irradiate light. The light radiated from the refractive optical system PEL may be reflected by the glass USS and collected again by the refractive optical system PEL. The refractive optical system PEL may inspect whether the glass USS is distorted through the collected light.

Figure 9D:
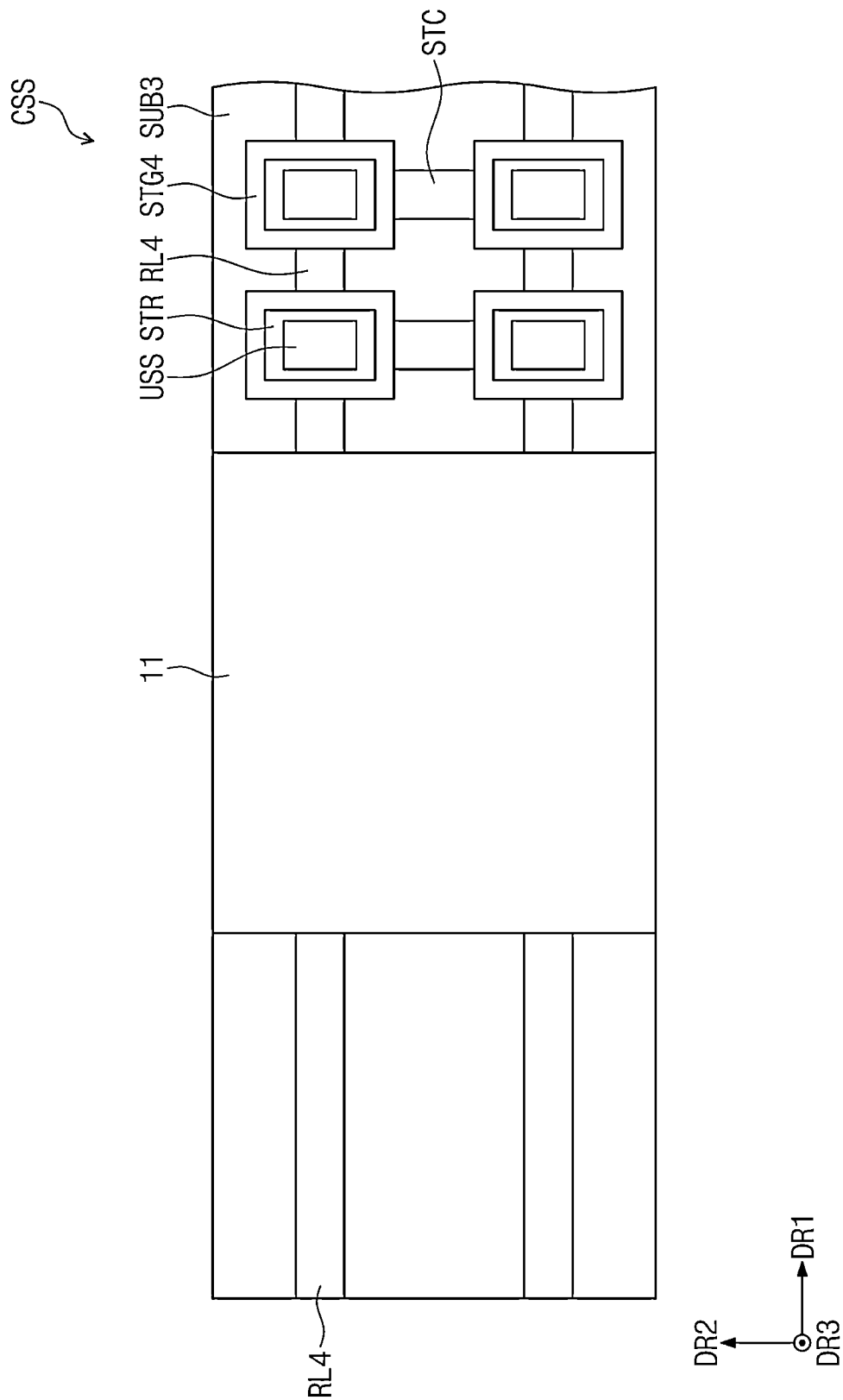

As shown in FIG. 9D, the glass USS after the distortion inspection may pass through the distortion inspection part 11 to move in the first direction DR1.

Figure 10:
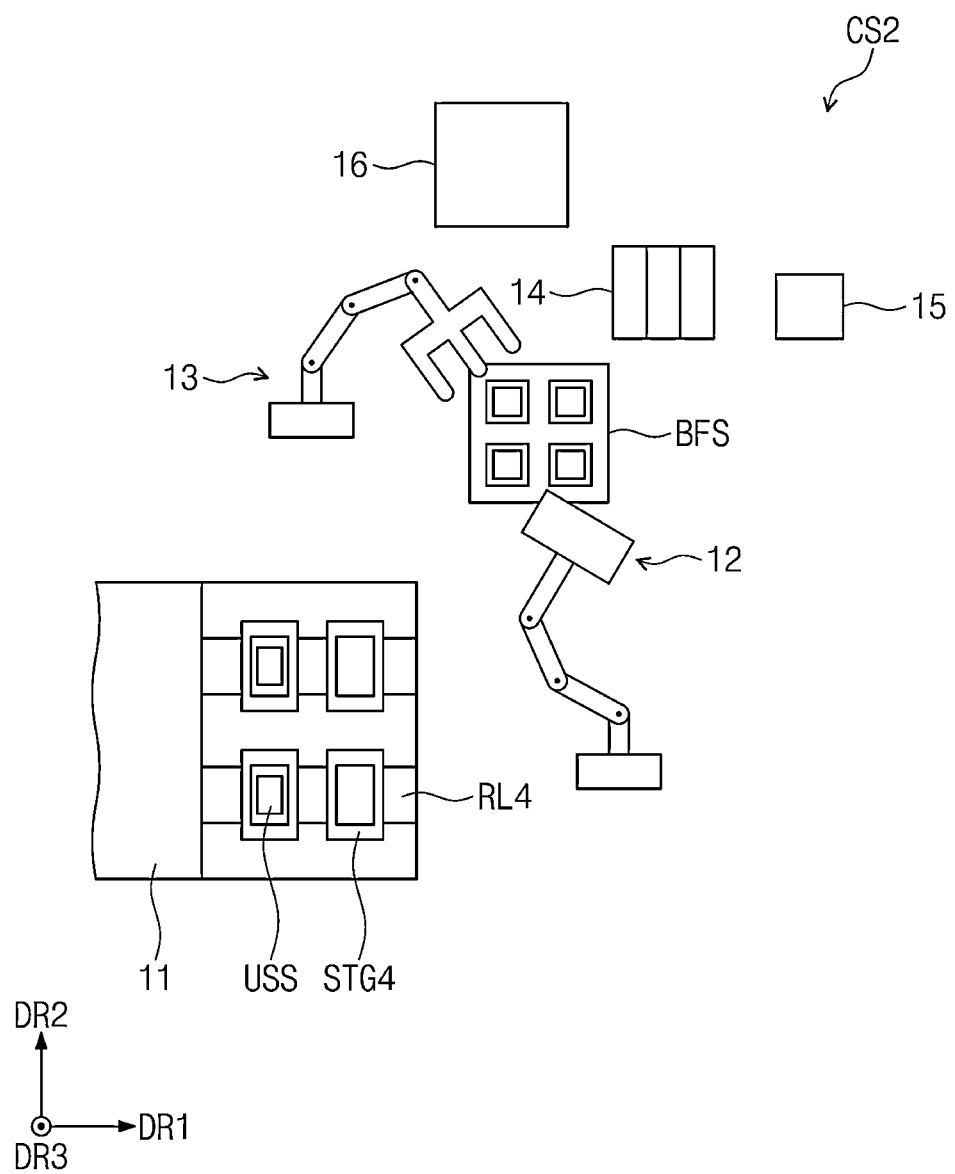
FIG. 10 is a plan view of a second crack inspection section.

FIG. 10 is a plan view of a second crack inspection section.

Referring to FIGS. 5 and 10, the second crack inspection section CS2 may include a fifth robot arm 12, a buffer stage BFS, a sixth robot arm 13, a second crack inspection part 14, a second disposal part 15, and a second glass accommodation part 16.

The fifth robot arm 12 of FIG. 10 is the same as the second robot arm 7 of FIGS. 7I and 7J, the sixth robot arm 13 of FIG. 10 is the same as the first robot arm 2 of FIGS. 6A and 6B, and the second crack inspection part 14 and the second disposal part 15, and the second glass accommodation part 16 are the same as the first crack inspection part 3, the first disposal part 4, and the first glass accommodation part 1 of FIG. 6A, and thus any repetitive detailed description thereof will be omitted or simplified.

Referring to FIG. 10, the glasses USS after the distortion inspection may be loaded on the buffer stage BFS by the fifth robot arm 12. When accommodating spaces of the glasses USS are saturated in the second glass accommodation part 16 to be described later, the glasses USS whose distortion inspection has been completed may stand by in the buffer stage BFS while the second glass accommodation part 16 is replaced.

The glass USS loaded on the buffer stage BFS may be transferred to the second crack inspection part 14 by the sixth robot arm 13. The second crack inspection part 14 may inspect the surface of the glass USS for cracks. The second crack inspection part 14 may inspect the presence or absence of cracks in the glass USS by radiating light. When cracks exist among the glasses USS inspected by the second crack inspection part 14, the glasses USS may be disposed or discarded in the second disposal part 15 adjacent to the second crack inspection part 14 and the sixth robot arm 13. When there is no crack in the glass USS, the sixth robot arm 13 may transfer the glasses USS to the second glass accommodation part 16.

According to an embodiment of the invention, the number of times of contact between the glass and the inspection equipment may be reduced. Accordingly, the possibility of scratching the glass may be reduced and a defect rate of the glass may be improved The invention should not be construed as being limited to the embodiments set forth herein. Rather, these embodiments are provided so that this disclosure will be thorough and complete and will fully convey the concept of the invention to those skilled in the art.

While the invention has been particularly shown and described with reference to embodiments thereof, it will be understood by those of ordinary skill in the art that various changes in form and details may be made therein without departing from the spirit or scope of the invention as defined by the following claims.

What is claimed is:

1. A glass inspection equipment comprising:
   a first transfer rail extending in a first direction, wherein a glass including first sides and second sides extending in a direction intersecting the first sides reciprocates in the first direction along the first transfer rail;
   a rotation part disposed on the first transfer rail, wherein the rotation part rotates the glass;

an edge inspection part disposed on the first transfer rail, wherein the edge inspection part inspects the first and second sides of the glass; and a surface inspection part which inspects a surface of the glass after an inspection of the first and second sides by the edge inspection part, wherein the edge inspection part inspects the first sides when the glass in a state where the first sides thereof are arranged parallel to the first direction is transferred under the edge inspection part, and wherein the edge inspection part inspects the second sides when the glass transferred through the edge inspection part to inspect the first side is rotated by the rotation part and the glass in a state where the second sides thereof are arranged parallel to the first direction is transferred under the edge inspection part.

2. The glass inspection equipment of claim 1, wherein the glass is reciprocally transferred in the first direction along the first transfer rail, and passes the edge inspection part at least twice.

3. The glass inspection equipment of claim 1, further comprising:
a first glass accommodation part on which the glass is loaded; and
a first robot arm which transfers the glass from the first glass accommodation part to the first transfer rail.

4. The glass inspection equipment of claim 3, further comprising:
a first crack inspection part adjacent to the first robot arm, wherein the first crack inspection part inspects a crack of the glass transferred by the first robot arm; and
a first disposal part adjacent to the first robot arm,
wherein, when the crack is detected in the glass, the glass is discarded in the first disposal part, and
wherein, when no crack is detected in the glass, the first robot arm transfers the glass to the first transfer rail.

5. The glass inspection equipment of claim 1, further comprising:
an alignment part which aligns the glass in the first direction and in a second direction intersecting the first direction; and
an alignment inspection part which inspects an alignment state of the glass,
wherein the alignment part is disposed between the first transfer rail and the rotation part.

6. The glass inspection equipment of claim 5, wherein the surface inspection part receives the glass aligned by the alignment part and inspects a scratch on the surface of the glass.

7. The glass inspection equipment of claim 6, further comprising:
a glass extension part disposed to overlap portions of the glass adjacent to opposing sides thereof, wherein the glass extension part extends the glass to be flat.

8. The glass inspection equipment of claim 7, wherein the surface inspection part includes:
a first surface inspection part which inspects a first surface of the glass not overlapping the glass extension part; and
a second surface inspection part which inspects a second surface of the glass overlapping the glass extension part after removing the glass extension part.

9. The glass inspection equipment of claim 8, further comprising:
a second robot arm which transfers the glass aligned by the alignment part to the first surface inspection part.

10. The glass inspection equipment of claim 8, further comprising:
a third robot arm which transfers the glass inspected by the first surface inspection part to the second surface inspection part.

11. The glass inspection equipment of claim 1, further comprising:
a distortion inspection part which inspects a distorted state of the glass after a surface inspection by the surface inspection part.

12. The glass inspection equipment of claim 11, further comprising:
a fourth robot arm which transfers the glass after the surface inspection to the distortion inspection part.

13. The glass inspection equipment of claim 11, wherein the distortion inspection part inspects the distorted state of the glass by radiating light to the glass and examining the light reflected from the glass.

14. The glass inspection equipment of claim 11, further comprising:
a stage disposed in each of the edge inspection part and the distortion inspection part,
wherein a folding area extending parallel to a second direction intersecting the first direction is defined in the glass, and
wherein a groove overlapping the folding area is defined on an upper surface of the stage.

15. The glass inspection equipment of claim 11, further comprising:
a buffer stage on which the glass is seated after an distortion inspection by the distortion inspection part.

16. The glass inspection equipment of claim 15, further comprising:
a fifth robot arm which transfers the glass after the distortion inspection to the buffer stage.

17. The glass inspection equipment of claim 15, further comprising:
a second glass accommodation part;
a sixth robot arm which transfers the glass disposed on the buffer stage to the second glass accommodation part;
a second crack inspection part adjacent to the sixth robot arm, wherein the second crack inspection part inspects a crack of the glass transferred by the sixth robot arm; and
a second disposal part adjacent to the sixth robot arm,
wherein, when the crack is detected in the glass, the glass in which the crack exists is discarded in the second disposal part, and
wherein, when no crack is detected in the glass, the sixth robot arm transfers the glass to the second glass accommodation part.

18. A method of inspecting a glass, the method comprising:
disposing a glass including first sides and second sides extending in a direction intersecting the first sides on a first transfer rail to allow the glass to reciprocate in a first direction along the first transfer rail;
inspecting the first and second sides using an edge inspection part when the glass is disposed under the edge inspection part disposed on the first transfer rail;
inspecting a surface of the glass using a surface inspection part after the inspecting the first and second sides; and
inspecting a distorted state of the glass using a distortion inspection part after the inspecting the surface of the glass, wherein the inspecting the first sides and the second sides includes:
    inspecting the first sides when the glass in a state where the first sides thereof are arranged parallel to the first direction is transferred under the edge inspection part;
    rotating the glass transferred through the edge inspection part in a way such that the second sides are arranged parallel to the first direction; and
    inspecting the second sides when the glass in a state where the second sides thereof are arranged parallel to the first direction is transferred under the edge inspection part.

19. The method of claim 18, further comprising:
extending the glass to be flat through a glass extension part disposed to overlap portions of the glass adjacent to opposing sides thereof,
wherein the inspecting the surface of the glass includes:
    inspecting a first surface of the glass not overlapping the glass extension part using a first surface inspection part of the surface inspection part; and
    inspecting a second surface of the glass overlapping the glass extension part, after removing the glass extension part using a second surface inspection part of the surface inspection part.

20. The method of claim 18, wherein the inspecting the distorted state of the glass includes examining light which is radiated and reflected on the glass.

* * * * *